United States Patent
Varol

(10) Patent No.: US 11,633,232 B2
(45) Date of Patent: Apr. 25, 2023

(54) DEVICE FOR INTERSTITIAL LASER THERAPY

(71) Applicant: Medlogical Innovations Pty Ltd, New South Wales (AU)

(72) Inventor: Celalettin Varol, New South Wales (AU)

(73) Assignee: MEDLOGICAL INNOVATIONS PTY LTD, New South Wales (AU)

( * ) Notice: Subject to any disclaimer, the term of this patent is extended or adjusted under 35 U.S.C. 154(b) by 356 days.

(21) Appl. No.: 16/096,331

(22) PCT Filed: Mar. 22, 2018

(86) PCT No.: PCT/AU2018/050262
§ 371 (c)(1),
(2) Date: Oct. 25, 2018

(87) PCT Pub. No.: WO2018/170549
PCT Pub. Date: Sep. 27, 2018

(65) Prior Publication Data
US 2020/0323589 A1    Oct. 15, 2020

(30) Foreign Application Priority Data

Mar. 23, 2017  (AU) .............................. 2017901030

(51) Int. Cl.
*A61B 18/20* (2006.01)
*A61B 18/00* (2006.01)
*A61B 18/22* (2006.01)

(52) U.S. Cl.
CPC .... *A61B 18/20* (2013.01); *A61B 2018/00797* (2013.01); *A61B 2018/00815* (2013.01);
(Continued)

(58) Field of Classification Search
CPC .......... A61B 18/20; A61B 2018/20357; A61B 2018/00797; A61B 2018/00815;
(Continued)

(56) References Cited

U.S. PATENT DOCUMENTS 5,758,663 A * 6/1998 Wilk ........................ A61B 1/05
606/1
6,056,745 A * 5/2000 Panescu ................. A61B 18/00
606/31
(Continued)

FOREIGN PATENT DOCUMENTS

| EP | 3058888 A1 | 8/2016 |
| FR | 3021520 A1 | 12/2015 |
| WO | 2009124301 A1 | 10/2009 |

OTHER PUBLICATIONS

International Search Report for corresponding international application No. PCT/AU2018/050262, dated Apr. 26, 2018.
(Continued)

*Primary Examiner* — Aaron F Roane
(74) *Attorney, Agent, or Firm* — Tarolli, Sundheim, Covell & Tummino LLP

(57) ABSTRACT

Disclosed is a device for interstitial laser therapy. The device comprises an optical waveguide extending about a central longitudinal axis and having an optical output end; an optical diffuser optically coupled to, optically associate with, or positioned about the optical output end, wherein the optical diffuser comprises a housing having an open end for receiving the optical output end and a first longitudinal portion of the optical waveguide; and a temperature sensor interposed, positioned or located between the central longitudinal axis and an exterior surface of the housing, and preferably within the longitudinal extent of the first longitudinal portion of the optical waveguide. The optical diffuser can be provided with one or more holes, one or more slits, one or more openings, and/or one or more vents. The device can also include a second temperature sensor. Also disclosed is a system for interstitial laser therapy.

26 Claims, 20 Drawing Sheets

(52) U.S. Cl.
CPC ............... *A61B 2018/00821* (2013.01); *A61B 2018/2005* (2013.01); *A61B 2018/206* (2013.01); *A61B 2018/20357* (2017.05); *A61B 2018/2211* (2013.01); *A61B 2018/2261* (2013.01); *A61B 2218/002* (2013.01)

(58) Field of Classification Search
CPC .. A61B 2018/00821; A61B 2018/2005; A61B 2018/206; A61B 2018/2211; A61B 2018/2261; A61B 2218/002
USPC .......................................................... 606/15
See application file for complete search history.

(56) References Cited

U.S. PATENT DOCUMENTS

| | | |
|---|---|---|
| 2001/0056278 A1 | 12/2001 | Nield et al. |
| 2008/0086160 A1* | 4/2008 | Mastri ................ A61B 17/3417 206/363 |
| 2008/0119694 A1* | 5/2008 | Lee ...................... A61B 5/0075 600/127 |
| 2009/0131931 A1 | 5/2009 | Lee et al. |
| 2011/0105824 A1 | 5/2011 | Krespi |
| 2012/0022510 A1 | 1/2012 | Welches et al. |
| 2013/0261621 A1 | 10/2013 | Kramer et al. |
| 2014/0088488 A1 | 3/2014 | Loeb |
| 2015/0057648 A1 | 2/2015 | Swift et al. |
| 2016/0206374 A1 | 7/2016 | Tyc et al. |

OTHER PUBLICATIONS

European Search Report for Application No. 18770419.2-112/3600107 PCT/AU2018050262 dated Jul. 24, 2020.
Singapore Search Report for Application No. 11201907525Y dated Dec. 21, 2020.
Sinapore Written Opinion for Application No. 11201907525Y dated Dec. 23, 2020.

* cited by examiner

DEVICE FOR INTERSTITIAL LASER THERAPY

RELATED APPLICATIONS

The present invention is a U.S. National Stage under 35 USC 371 patent application, claiming priority to Serial No. PCT/AU2018/050262, filed on 22 Mar. 2018; which claims priority of AU 2017901030, filed on 23 Mar. 2017, the entirety of both of which are incorporated herein by reference.

TECHNICAL FIELD

The present invention generally relates to the field of interstitial laser thermotherapy. In further specific examples, a temperature sensor is formed or provided as part of a device for interstitial laser therapy.

BACKGROUND

Optical fibres exhibit excellent light-guiding properties which, combined with a compact size and flexibility, make them ideal for various medical applications.

Interstitial laser therapy is one such application, in which light is directed at a target tissue to induce local hyperthermia and destroy the tissue. Interstitial laser therapy can be effective for treating lesions and tumours, particularly those difficult to access using conventional surgery.

Interstitial techniques of local hyperthermia deep inside a patient's body offer a safe and effective way of treating cancers. Tumours can be accessed via a cannula, minimising the invasiveness of the procedure and improving patient comfort while reducing side effects.

A key challenge in interstitial laser therapy involves monitoring and controlling the temperature of the target area during treatment. Hyperthermia is capable of destroying both tumour tissue as well as any surrounding healthy tissue.

It has been well established that heating tissue to 60° C. for one minute induces irreversible cell death. At 100° C., tissue destruction is immediate. Typically, the aim of thermotherapy is to induce local hyperthermia and coagulative necrosis in a target tissue, without causing charring. It is therefore critical that the temperature of the target area be continuously monitored during interstitial laser therapy, to provide real-time feedback on the status of the target area.

Advanced medical imaging devices such as magnetic resonance imaging (MRI) scanners, with the aid of external computer interfaces, may be used to estimate internal temperatures during interstitial laser therapy. These devices however are expensive, bulky, and their operation necessitates extensive training. Moreover, the temperature readings they provide are not direct measurements but have to be extrapolated by a computer and can therefore suffer from low accuracy.

The lack of rapid and reliable feedback concerning the tissue's temperature means that current thermotherapy devices necessitate cooling systems to minimise the risk of charring the tissue. Example cooling systems include cooling or irrigation catheters. These cooling systems however increase the overall size of the accessing cannula, inducing greater trauma to the patient.

There is a need for new or improved devices and/or systems for interstitial laser therapy.

The reference in this specification to any prior publication (or information derived from the prior publication), or to any matter which is known, is not, and should not be taken as an acknowledgment or admission or any form of suggestion that the prior publication (or information derived from the prior publication) or known matter forms part of the common general knowledge in the field of endeavour to which this specification relates.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to example aspects, there is provided a device and/or a system for interstitial laser therapy. The device preferably comprises an optical waveguide having an optical output end, and an optical diffuser optically coupled to the optical output end. In one example form, the optical diffuser comprises a housing having an open end for receiving the optical output end. In another example form, the optical diffuser comprises a housing having an open end for receiving a longitudinal portion of the optical waveguide. Preferably, the optical diffuser comprises a housing having an open end for receiving the optical output end and the longitudinal portion of the optical waveguide. In another example form, the device includes a temperature sensor. Preferably, the temperature sensor is interposed, or positioned or located, between a central longitudinal axis of the optical waveguide and an exterior surface of the housing, and optionally within the longitudinal extent of the longitudinal portion of the optical waveguide.

According to one example aspect, there is provided a device for interstitial laser therapy comprising: an optical waveguide having an optical output end; an optical diffuser optically coupled to, or is optically associated with, or is positioned about, the optical output end, wherein the optical diffuser comprises an open end for receiving the optical output end; and a temperature sensor positioned internally of an exterior surface of the optical diffuser.

According to another example aspect, there is provided a device for interstitial laser therapy comprising: an optical waveguide extending about a central longitudinal axis and having an optical output end; an optical diffuser optically coupled to the optical output end, wherein the optical diffuser comprises a housing having an open end for receiving the optical output end and a longitudinal portion of the optical waveguide; and a temperature sensor interposed between the central longitudinal axis and an exterior surface of the housing within the longitudinal extent of the longitudinal portion of the optical waveguide.

According to another example aspect, there is provided a system for interstitial laser therapy comprising: one of the devices for interstitial laser therapy described above; a power-tunable optical source optically coupled to the optical waveguide; and a processing system configured to: obtain a temperature measurement from the temperature sensor; and adjust an optical output power of the optical source.

BRIEF DESCRIPTION OF FIGURES

Example embodiments are apparent from the following description, which is given by way of example only, of at least one non-limiting embodiment, described in connection with the accompanying figures.

DETAILED DESCRIPTION

Figure 1:
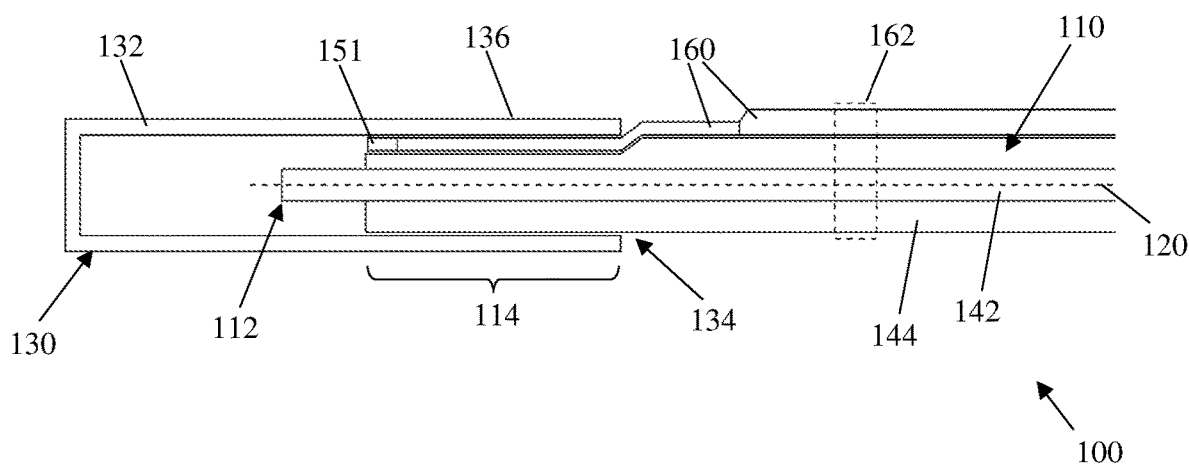
FIG. 1 illustrates a cross-sectional view of an example device for interstitial laser therapy, from a front-side perspective.

The following modes, given by way of example only, are described in order to provide a more precise understanding of the subject matter of an embodiment or embodiments. In the figures, incorporated to illustrate features of an example embodiment, like reference numerals are used to identify like parts throughout the figures.

In the context of this specification, the term "about" is understood to refer to a range of numbers that a person of skill in the art would consider equivalent to the recited value in the context of achieving the same function or result.

Figure 2:
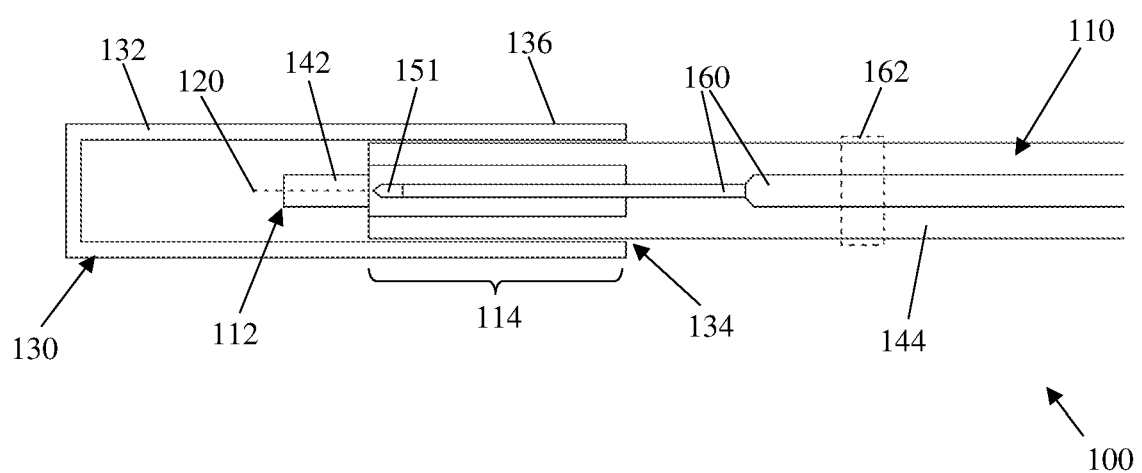
FIG. 2 illustrates a cross-sectional view of the device of FIG. 1, from a top-side perspective.

Referring to FIGS. 1 and 2, there is provided an example device 100 for interstitial laser therapy. Device 100 includes an optical waveguide 110 extending about a central longitudinal axis 120 and having an optical output end 112. Output end 112 is a distal end of optical waveguide 110. Device 100 further includes an optical diffuser 130 optically coupled to, or optically associated with, or positioned about, output end 112. Diffuser 130 includes, or is comprised of, a housing 132 having an open end 134 for receiving output end 112, and preferably for also receiving a longitudinal portion 114 of optical waveguide 110. Housing 132 has an exterior surface 136, for example being a circumferential exterior surface. Device 100 further includes a temperature sensor 151. Temperature sensor 151 is preferably positioned internally of exterior surface 136 of optical diffuser 130. In one example, temperature sensor 151 is interposed, or positioned, or located, between central longitudinal axis 120 and exterior surface 136, furthermore temperature sensor 151 is preferably, though not necessarily, also interposed, or positioned, or located, within the longitudinal extent of longitudinal portion 114 of optical waveguide 110.

Central longitudinal axis 120 is an imaginary axis centred on, or coinciding to, a main path of propagation of electromagnetic waves in optical waveguide 110. In some examples, where optical waveguide 110 comprises multiple paths of propagation of electromagnetic waves, central longitudinal axis 120 is centred on, or coincides to, a central path of propagation of electromagnetic waves.

Thus, in one example there is provided a device 100 for interstitial laser therapy comprising an optical waveguide 110 having an optical output end 112. An optical diffuser 130 is optically coupled to, or is optically associated with, or is positioned about, the optical output end 112, wherein the optical diffuser 130 comprises an open end 134 for receiving the optical output end 112. A temperature sensor 151 is positioned internally of an exterior surface 136 of the optical diffuser 130.

Figure 5:
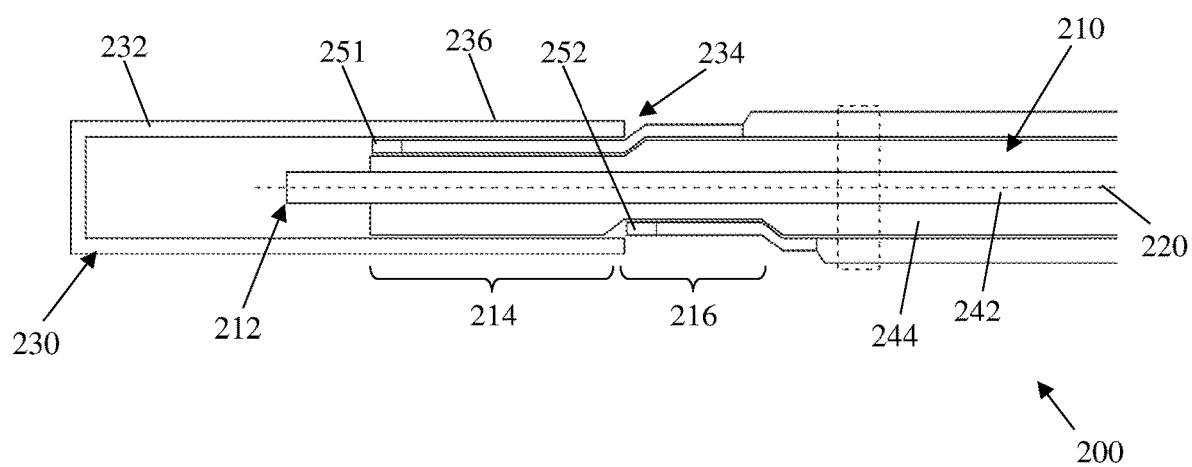
FIG. 5 illustrates a cross-sectional view of a further example device for interstitial laser therapy, from a front-side perspective.

The central longitudinal axis 120 does not intersect with, or pass through, first temperature sensor 151 (and/or a second temperature sensor, if provided, such as second temperature sensor 252 of FIG. 5). First temperature sensor 151 (and/or a second temperature sensor, if provided, such as second temperature sensor 252 of FIG. 5) is positioned apart from the optical output end 112. First temperature sensor 151 can be positioned adjacent to and/or abutting an internal surface of optical diffuser 130.

Preferably, though not necessarily, optical waveguide 110 is an optical fibre, or is a plurality of optical fibres. Examples of suitable optical fibres include quartz optical fibres, although any other material suitable for propagation of electromagnetic waves may also be suitable, such as silica, fluoride glass, phosphate glass, chalcogenide glass, polymers, or any other material.

The dimensions of the optical fibre may vary depending on particular applications of device 100. In one example, the optical fibre has a diameter of about 600 µm and a divergence angle of about 8°. In other examples, the optical fibre may have any other suitable diameter size and divergence angle. These dimensions may depend on the size of the lesion or tumour requiring treatment. For example, when treating larger tumours, it may be preferable for the optical fibre to have a larger diameter size and/or a greater divergence angle spread since, with these characteristics, device 100 may achieve a larger thermal imprint and destruction of tissue over a wider area.

In other examples, optical waveguide 110 may be any type of optical waveguide or collection of optical waveguides. Examples of suitable optical waveguides include but are not limited to: single mode fibres, multi-mode fibres, optical cables comprising one or more optical fibres, planar waveguides, and strip waveguides.

Preferably, though not necessarily, optical waveguide 110 is capable of guiding electromagnetic waves having a wavelength, or range of wavelengths, in the visible (400 nm to 700 nm) and/or infrared (700 nm to 1 mm) spectra. In some examples, optical waveguide 110 is suitable for guiding electromagnetic waves having wavelengths in the range between about 890 nm and about 960 nm.

Optical waveguide 110 includes an inner layer 142 and an outer layer 144 radially surrounding inner layer 142. Inner layer 142 is for guiding electromagnetic waves (e.g. visible and/or infrared radiation) and comprises a core layer and a cladding layer (not shown) radially surrounding the core layer. Outer layer 144 is for protecting inner layer 142 and comprises a protective jacket. In other examples, optical waveguide 110 may have additional or fewer layers. For example, optical waveguide 110 may include two or more protective jacket layers, or it may have no projective jacket layer.

Output end 112 is preferably stripped of outer layer 144. This may be advantageous for preventing outer layer 144 from being exposed to electromagnetic radiation, which may cause outer layer 144 to burn and damage optical waveguide 110. In some examples, output end 112 has a longitudinal length of about 1.7 mm. That is, optical waveguide 110 is stripped of outer layer 144 along a longitudinal portion extending from the tip of output end 112 for about 1.7 mm. In some examples, output end 112 has a longitudinal length extending between about 1 mm and about 2 mm. In other examples, output end 112, or a longitudinal portion of output end 112, may be stripped of outer layer 144 along any other longitudinal length. Alternatively, output end 112 may not be stripped of outer layer 144, or it may be partially stripped of outer layer 144, or only a radial portion of outer layer 144 may be stripped or shaved from output end 112.

The tip, or longitudinal extremity, of output end 112 is cleaved or polished flat. In other examples, output end 112 may have an angled tip (i.e. cleaved at an angle relative to longitudinal axis 120), a cone tip, a ball tip, or any other geometry or termination configuration.

Optical waveguide 110 may further include an optical input end (not shown) which is adapted to receive electromagnetic waves outputted from an optical source such as a laser or light-emitting diode (LED). The optical input end may be provided with a connector for coupling with an optical output port of the optical source. During operation, electromagnetic waves entering the optical input end propagate through optical waveguide 110 along its longitudinal axis 120 and exit from output end 112.

Diffuser 130 is optically coupled to, or optically associated with, or positioned about, output end 112 such that electromagnetic waves exiting output end 112 propagate into diffuser 130. Electromagnetic waves entering diffuser 130 from output end 112 are diffused, scattered, or spread across the surface area of housing 132.

The use of an optical diffuser improves the operation of device 100 for the purpose of interstitial laser therapy. Without the use of an optical diffuser, the energy outputted by an optical waveguide is typically concentrated in a narrow spot. Such high energy concentration can cause tissue in the vicinity of the output end of the waveguide to char or vaporize. While it is possible to create large thermal lesions in this manner, the morphology of the resulting lesion is highly unpredictable and not reproducible. The use of an optical diffuser causes the energy outputted by the optical waveguide to be distributed across a larger surface area, resulting in more tempered coagulation across larger volumes, while minimising or preventing charring of tissue. The use of an optical diffuser permits more consistent and predictable treatment procedures. Moreover, an optical diffuser limits denaturing of the optical waveguide tip. Preservation of the optical waveguide tip allows for repeated use of device 100, as well as enhancing its safety and accuracy.

In one example, housing 132 is cylindrical or tubular. In other examples, housing 132 may have any other geometry, such as conical. Moreover, diffuser 130 may be hollow or diffuser 130 may further include scattering material enclosed by housing 132 and forming a medium for scattering of electromagnetic waves entering diffuser 130.

Housing 132 is preferably a tubular housing comprising an open end 134, a closed end opposite open end 134, and an exterior surface 136. Open end 134 is mechanically coupled to, or is fixed to, or is attached to, longitudinal portion 114. A longitudinal portion of housing 132 surrounds longitudinal portion 114 and clasps to, or embraces, or grips, or frictionally engages with, outer layer 144. In some examples, glue or other fastening mechanisms may be provided to mechanically couple, or fix, or attach, housing 132 to longitudinal portion 114.

Housing 132 is defined by an inner diameter, being the diameter of a receptacle (i.e. the space for receiving output end 112 and longitudinal portion 114) of housing 132, and an outer diameter, being the diameter of exterior surface 136 of housing 132. The inner diameter of housing 132 is substantially equal to an outer diameter of optical waveguide 110. In this case, the outer diameter of housing 132 is greater than an outer diameter of optical waveguide 110, such that diffuser 130 bulges, or protrudes, radially outward relative to optical waveguide 110.

In other examples, the outer diameter of housing 132 is approximately equal to the outer diameter of optical waveguide 110, such that diffuser 130 is level with optical waveguide 110. In this last example, housing 132 has a smaller inner diameter than the outer diameter of optical waveguide 110. Therefore, outer layer 144 of longitudinal portion 114 may need to be shaved, or partially stripped, so as to allow longitudinal portion 114 to be received into housing 132. An advantage of this last example is that the coupling of diffuser 130 to optical waveguide 110 does not increase the diameter of device 100.

In yet other examples, the outer diameter of housing 132 may be less than the outer diameter of optical waveguide 110.

Housing 132 is composed of a light-transmissive material to allow electromagnetic radiation scattered within diffuser 130 to radiate into a tissue being treated. Preferably, though not necessarily, housing 132 is composed of a heat resistant material (for example, a material having a low coefficient of thermal expansion), able to withstand temperatures up to at least about 100° C., or any maximum temperature that may be required for interstitial laser therapy.

Preferably, though not necessarily, housing 132 comprises polytetrafluoroethylene (PTFE), also known as "Teflon". Advantageously, PTFE can be heat resistant up to about 300° C. In other examples, other light transmissive materials may compose housing 132, such polycarbonate, polyurethane, polyethylene, polypropylene, silicon, nylon, PVC, PET, ABS, PES, PEEK, FEP, as well as other flexible or rigid, radio-opaque or non radio-opaque materials as appropriate.

An optical diffuser made from a heat-resistant material, such as PTFE, is advantageous since it enables coagulation of the tissue being treated without charring, and it protects the tip of the optical waveguide from melting or burning during treatment. Moreover, a heat-resistant diffuser removes the need for cooling systems for preserving the integrity of device 100. Therefore, device 100 need not include a cooling system.

Temperature sensor 151 is provided for measuring the temperature of a tissue being treated through interstitial thermal therapy by device 100. Therefore, device 100 allows for laser interstitial thermal therapy of tumours or tissues located in the liver, pancreas, prostate, brain, or any other location within a patient's body. In addition, device 100 allows for precise, direct, and fast measurement of absolute or relative temperatures of the tumour or tissue being treated. The temperature readings provided by temperature sensor 151 are useful for regulating the amount of radiation delivered to the tissue by device 100, and for obtaining or maintaining the necessary therapeutic tissue temperature.

Temperature sensor 151 is interposed, radially interposed, or enclosed, or positioned, or located, between, or at least partially between, central longitudinal axis 120 and exterior surface 136 of housing 132. Preferably, temperature sensor 151 is also interposed, or positioned, or located, within the longitudinal extent of longitudinal portion 114 of the optical waveguide 110. In another example, temperature sensor 151 is positioned internally of exterior surface 136 of the optical diffuser 130. Central longitudinal axis 120 does not intersect with, or pass through, first temperature sensor 151. First temperature sensor 151 is positioned apart from, or away from, or does not abut, optical output end 112. First temperature sensor 151 can be positioned adjacent to and/or abutting an internal surface of optical diffuser 130. Longitudinal portion 114 is a longitudinal portion, segment, or section of waveguide 110, which is interior to housing 132 (i.e. housing 132 is mechanically coupled to longitudinal portion 114, or is mechanically coupled to at least part of longitudinal portion 114). The length of longitudinal portion 114 may vary depending on the internal structure of housing 132, into which longitudinal portion 114 is received. Preferably, though not necessarily, longitudinal portion 114 is directly adjacent to, or near, output end 112. In some examples, longitudinal portion 114 extends from a point of output end 112 stripped of outer layer 144.

In some examples, the length of longitudinal portion 114 is about 5 mm, meaning that the distance from an extremity of output end 112 stripped of outer layer 144 and a point of optical waveguide 110 near open end 134, is about 5 mm. In other examples, the length of longitudinal portion 114 is about 3 mm, or is about 4 mm, or is about 6 mm, or is about 7 mm, or is about 8 mm. In other examples, the length of longitudinal portion 114 is between about 1 mm and about 10 mm. In other examples, the length of longitudinal portion 114 is between about 2 mm and about 8 mm. In other examples, the length of longitudinal portion 114 is between about 3 mm and about 7 mm. In other examples, the length of longitudinal portion 114 is between about 4 mm and about 6 mm. In other examples, longitudinal portion 114 may have any suitable length.

Figure 3:
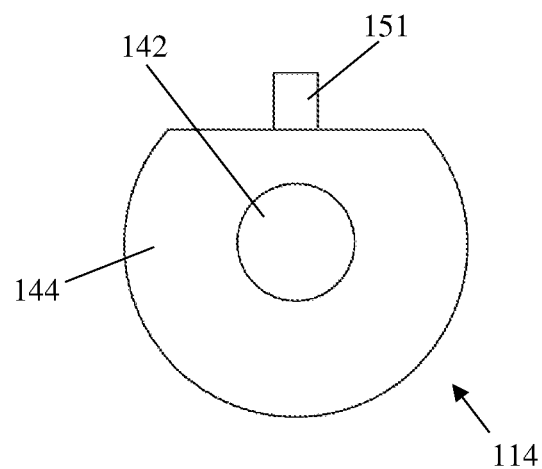
FIG. 3 illustrates a cross-sectional view of a longitudinal portion of the device of FIG. 1.

Longitudinal portion 114 is at least partially stripped of outer layer 144 for accommodating temperature sensor 151. A recess, groove, or indentation, is formed within outer layer 144 and temperature sensor 151 is arranged, located, or positioned within this recess. A cross-sectional view of longitudinal portion 114 is illustrated in FIG. 3, illustrating the profile of the recess, groove, or indentation for accommodating temperature sensor 151. Other recess profiles may also be used, for example, recess profiles that closely conform, or comport, to the profile of temperature sensor 151. In other examples, temperature sensor 151 is embedded within outer layer 144 of longitudinal portion 114.

Figure 4:
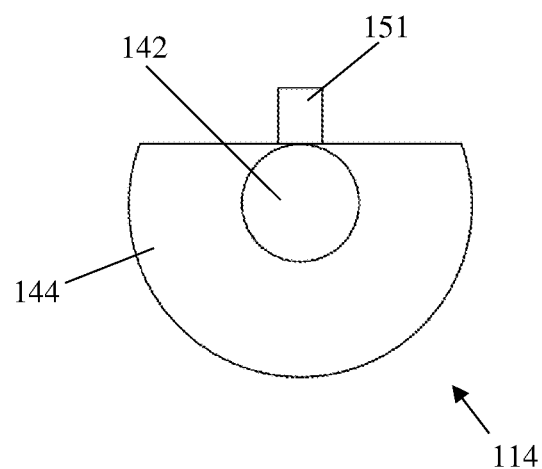
FIG. 4 illustrates a cross-sectional view of a longitudinal portion of an alternative embodiment of the device of FIG. 1.

The recess for accommodating temperature sensor 151 may be formed by etching a portion, or slice, of outer layer 144 in longitudinal portion 114. The depth of the recess is such that temperature sensor 151 is in contact with, or attaches to, a remaining strip of outer layer 144 in longitudinal portion 114. In other examples, illustrated in FIG. 4, the depth of the recess is such that temperature sensor 151 is in contact with, or attaches to, an exposed portion of inner layer 142. For example, temperature sensor 151 may be in contact, or attached to, an exposed portion of a cladding or core layer of optical waveguide 110. The recess may therefore be formed by fully etching, or stripping, outer layer 144 along a segment of longitudinal portion 114. In some examples, the recess has a maximum depth of about 0.3 mm deep. In other examples, the recess has a maximum depth less than about 1 mm, or about 2 mm, or any other suitable maximum depth value.

In some examples, temperature sensor 151 may adhere to optical waveguide 110 with an adhesive, for example a cyanoacrylate-based adhesive. In other examples, any other mechanism of securely fixing or attaching temperature sensor 151 to optical waveguide 110 may be utilised.

Preferably, though not necessarily, the depth of the recess is such that temperature sensor 151 does not project, or protrude, past the outer diameter, or outer extent, of optical waveguide 110.

Preferably, though not necessarily, temperature sensor 151 is a micro-temperature sensor, or a temperature sensor having dimensions comporting with characteristic cross-sectional dimensions of optical waveguide 110. In some examples, the characteristic cross-sectional dimensions of optical waveguide 110 are in a millimetre or sub-millimetre range, such as between about 0.06 mm to about 0.1 mm. In some examples, temperature sensor 151 is an integrated temperature sensor, including an integrated circuit for the purpose of measuring temperature.

In some examples, temperature sensor 151 is a thermocouple or a microthermocouple. In other examples, temperature sensor 151 is an infrared temperature sensor. In other examples, temperature sensor 151 is a fully integrated microelectromechanical system (MEMs) thermopile sensor capable of measuring the temperature of an object without having to be in direct contact, such as the Texas Instruments TMP006 or TMP006B infrared thermopile contactless temperature sensor. In other examples, other types of temperature sensors may be used, such as digital temperature sensors, analog temperature sensors, electrical temperature sensors, mechanical temperature sensors, thermistors, silicon bandgap temperature sensors, or any other type of temperature sensor.

In one example, temperature sensor 151 connects to electrical cable, or lead, 160 necessary for the operation of temperature sensor 151 (e.g. for powering temperature sensor 151 and/or for transmitting measurement data). Electrical cables 160 extend along optical waveguide 110 to reach an operator or system for operating device 100. Preferably, though not necessarily, cables 160 may be fastened to optical waveguide 110 to avoid them becoming tangled during operation of device 100. In some examples, fluorine tape windings 162 may fasten these electrical cables to optical waveguide 110. In other examples, other fastening mechanisms may be used.

In other examples, temperature sensor 151 is a wireless temperature sensor, transmitting its temperature measurements by way of a wireless link. In some examples, temperature sensor 151 is a wireless temperature sensor that is powered wirelessly. An example wireless temperature sensor is that developed by the Mixed-Signal Microelectronics group at Eindhoven University of Technology, which is powered by radio waves that are part of a wireless network of the sensor. Further examples of suitable wireless temperature sensors may be found in Hao Gao's PhD thesis "Fully integrated ultra-low power mm-wave wireless sensor design methods" and in the publication of Hao Gao et al., "A 71 GHz RF energy harvesting tag with 8% efficiency for wireless temperature sensors in 65 nm CMOS," 2013 IEEE Radio Frequency Integrated Circuits Symposium (RFIC), Seattle, Wash., 2013, pp. 403-406. In example embodiments where temperature sensor 151 is a wireless sensor, or in other examples where cables 160 are superfluous, cables 160 may not be included in device 100.

Preferably, though not necessarily, temperature sensor 151 is adapted to measure temperature external to optical diffuser 130. For example, where temperature sensor 151 is an infrared temperature sensor, its orientation should be set, or arranged, to detect an infrared energy spectrum of tissue being treated. Alternatively, temperature sensor 151 is adapted to measure a temperature external to optical diffuser 130 by measuring the temperature of optical diffuser 130. For example, optical diffuser 130 may be in contact with, or close proximity to, a tissue being treated, in which case optical diffuser 130 may be approximately in thermal equilibrium, or quasi-equilibrium, with the tissue.

In general, it is not desirable for temperature sensor 151 to be exposed to electromagnetic radiation exiting output end 112. Such exposure may lead to temperature sensor 151 absorbing the electromagnetic radiation, causing damage or erroneous temperature measurements. To avoid this, temperature sensor 151 is arranged, positioned, or located on longitudinal portion 114, which is itself removed, offset, or displaced, from a path of propagation of electromagnetic waves exiting output end 112.

In some examples, temperature sensor 151 is arranged, positioned, or located outside the range of electromagnetic exposure from output end 112. For example, temperature sensor 151 may be arranged further than a minimum distance from output end 112. In some examples, the position of temperature sensor 151 may be varied to prevent direct exposure to radiation depending on the operating conditions of device 100.

However, to enhance the accuracy of temperature measurements, it may be preferable to locate temperature sensor 151 as near as possible to tissue being irradiated by device 100. Therefore, in some examples, temperature sensor 151 should be as near as possible to output end 112 without being exposed to electromagnetic radiation exiting output end 112. In the example embodiment illustrated in FIGS. 1 and 2, temperature sensor 151 is arranged, positioned, or located at an extremity of longitudinal portion 114 near to, or in vicinity of, output end 112.

In other examples, device 100 further includes electromagnetic shielding for protecting temperature sensor 151 from exposure to electromagnetic waves outputted by output end 112 and/or reflected or scattered from diffuser 130. In this way, the temperature measurement is not affected, or is minimally affected, by direct absorbance of electromagnetic energy by temperature sensor 151.

Referring to FIG. 5, there is illustrated a further example device 200 for interstitial laser therapy. Device 200 includes an optical waveguide 210 extending about a central longitudinal axis 220 and having an optical output end 212. Device 200 further includes an optical diffuser 230 optically coupled to, or optically associated with, or positioned about, output end 212. Diffuser 230 includes a housing 232 having an open end 234 for receiving output end 212 and a first longitudinal portion 214 of optical waveguide 210. Device 200 further includes a first temperature sensor 251, interposed, positioned or located between longitudinal axis 220 and an exterior surface 236 of housing 232, within the longitudinal extent of the first longitudinal portion 214 of optical waveguide 210, and a second temperature sensor 252, attached to or fixed to optical waveguide 210. As previously, in another example, first temperature sensor 251 can be positioned internally of an exterior surface 236 of the optical diffuser 230.

Preferably, though not necessarily, second temperature sensor 252 is arranged, positioned, or located on optical waveguide 210 and externally to optical diffuser 230. Second temperature sensor 252 is attached or fixed within a second longitudinal portion 216 of optical waveguide 210. Second temperature sensor 252 is arranged, positioned, or located adjacent to open end 234 of optical diffuser 230. Second temperature sensor 252 is longitudinally offset, or displaced from first temperature sensor 251. In some examples, first temperature sensor 251 and second temperature sensor 252 are longitudinally offset by about 5 mm. In some examples, first temperature sensor 251 and second temperature sensor 252 are longitudinally offset by between about 4 mm to about 6 mm, or by between about 3 mm to about 7 mm, or by between about 2 mm to about 8 mm. In other examples, any length of longitudinal offset may be used between first and second temperature sensors 251 and 252.

Moreover, although first temperature sensor 251 and second temperature sensor 252 are illustrated as being located on circumferentially opposite ends of optical waveguide 210, this is not necessary. In other examples, any relative circumferential displacement between first temperature sensor 251 and second temperature sensor 252 may be used. Central longitudinal axis 120 does not intersect with, or pass through, first temperature sensor 251 and/or second temperature sensor 252. First temperature sensor 251 and/or second temperature sensor 252 are/is positioned apart from optical output end 212. First temperature sensor 251 can be positioned adjacent to and/or abutting an internal surface of optical diffuser 230. Second temperature sensor 252 can be positioned outside the longitudinal extent of optical diffuser 230, i.e. within second longitudinal portion 216.

Optical waveguide 210 includes an inner layer 242 and an outer layer 244 radially surrounding inner layer 242. Second longitudinal portion 216 is a longitudinal portion, segment, or section of optical waveguide 210, which is exterior to housing 232. Preferably, though not necessarily, second longitudinal portion 216 is in the immediate vicinity of, or directly adjacent to, housing 232. Second longitudinal portion 216 may have any longitudinal length, such as 1 mm, 2 mm, 3 mm, 4 mm, 5 mm, or any other length. Preferably, second longitudinal portion 216 does not overlap, or is not coextensive with, first longitudinal portion 214.

Second longitudinal portion 216 is at least partially stripped of outer layer 244 for accommodating second temperature sensor 252. A recess, groove, or indentation, is formed within outer layer 244 and second temperature sensor 252 is arranged, located, or positioned within this recess. In other examples, second temperature sensor 252 is embedded within outer layer 244 of second longitudinal portion 216.

Figure 6:
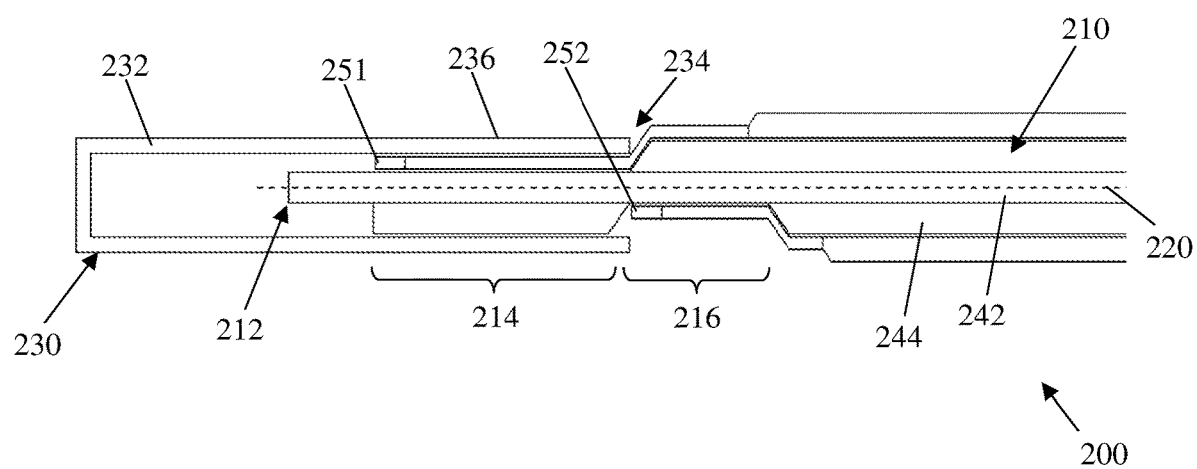
FIG. 6 illustrates a cross-sectional view of an alternative embodiment of the device of FIG. 5, from a front-side perspective.

The recess for accommodating second temperature sensor 252 may be formed by etching a portion, or slice, of outer layer 244 in second longitudinal portion 216. The depth of the recess is such that second temperature sensor 252 is in contact with, or attaches to, a remaining strip of outer layer 244 in second longitudinal portion 216. In other examples, illustrated in FIG. 6, the depth of the recess is such that second temperature sensor 252 is in contact with, or attaches to, an exposed portion of inner layer 242. As illustrated in FIG. 6, first temperature sensor 251 may also be in contact with, or attached to, an exposed portion of inner layer 242. That is, the recesses for accommodating first and second temperature sensors 251 and 252 may be formed by fully etching, or stripping, outer layer 244 along segments of first and second longitudinal portions 214 and 216.

In some examples, the recess has a maximum depth of about 0.3 mm deep. In other examples, the recess has a maximum depth less than about 1 mm. In other examples, the recess may have any other maximum depth value. In other examples, second temperature sensor 252 is arranged, located, or positioned within a cladding layer of inner layer 242, without obstructing the propagation of electromagnetic waves in a core layer of inner layer 242.

In some examples, second temperature sensor 252 may be attached to optical waveguide 210 with an adhesive, for example a cyanoacrylate based adhesive. In other examples, any other mechanism of securely fixing or attaching second temperature sensor 252 to optical waveguide 210 may be utilised.

Preferably, though not necessarily, the depth of the recess is such that second temperature sensor 252 does not project, or protrude, past the outer diameter of optical waveguide 210.

Preferably, though not necessarily, second temperature sensor 252 is a micro-temperature sensor, or a temperature sensor having dimensions comporting with characteristic cross-sectional dimensions of optical waveguide 210 (e.g. millimetre or sub-millimetre). In some examples, second temperature sensor 252 is an integrated temperature sensor, including an integrated circuit for the purpose of measuring temperature.

In some examples, second temperature sensor 252 is a thermocouple or a microthermocouple. In other examples, second temperature sensor 252 is an infrared temperature sensor. In other examples, second temperature sensor 252 is a fully integrated microelectromechanical system (MEMs) thermopile sensor capable of measuring the temperature of an object without having to be in direct contact, such as the Texas Instruments TMP006 or TMP006B infrared thermopile contactless temperature sensor. In other examples, other types of temperature sensors may be used, such as digital temperature sensors, analog temperature sensors, electrical temperature sensors, mechanical temperature sensors, thermistors, silicon bandgap temperature sensors, or any other type of temperature sensor.

In other examples, second temperature sensor 252 is a wireless temperature sensor, transmitting its temperature measurements by way of a wireless link. In some examples, second temperature sensor 252 is a wireless temperature sensor that is powered wirelessly, as previously described.

Furthermore, in some examples, second temperature sensor 252 is of a same type or kind as first temperature sensor 251. For example, both first temperature sensor 251 and second temperature sensor 252 may be microthermocouples. In other examples, second temperature sensor 252 is of a different type or kind compared to first temperature sensor 251. For example, first temperature sensor 251 may be an infrared temperature sensor and second temperature sensor 252 may be a microthermocouple. In other examples, first temperature sensor 251 and second temperature sensor 252 may have the same or different operational characteristics (e.g. temperature measurement range, measurement resolution) and ratings.

During operation of device 200, first temperature sensor 251 and second temperature sensor 252 measure or sense different temperatures. First temperature sensor 251 is provided to measure a temperature of a tissue being irradiated for the purpose of interstitial laser therapy, while second temperature sensor 252 is provided to measure temperatures of other objects and/or tissues. Since second temperature sensor 252 is offset from diffuser 230, it is not adapted to measure a temperature of a tissue being irradiated. In some examples, second temperature sensor 252 is adapted to measure a temperature external to optical diffuser 230. In some examples, second temperature sensor 252 provides a reference, or baseline, temperature reading. For example, second temperature sensor 252 may measure the temperature of a tissue adjacent to, surrounding, or in the vicinity of a tissue being treated. The temperature measurement of first temperature sensor 251 may then be considered relative to the temperature measurement of second temperature sensor 252. For example, device 200 may provide a measure of a temperature gradient, or difference, between first temperature sensor 251 and second temperature sensor 252. In some examples, first temperature sensor 251 and second temperature sensor 252 are adapted to measure a temperature difference.

In other examples, second temperature sensor 252 may be used to monitor temperatures of tissues which should not be heated during interstitial thermal therapy. For example, second temperature sensor 252 enables an operator to monitor the temperature of healthy tissue surrounding a tumour being treated, and to make appropriate adjustments in case the temperature of the healthy tissue surpasses a certain safe level. Alternatively, second temperature sensor 252 provides a backup, redundant, or alternative temperature sensor in case first temperature sensor 251 becomes unusable or faulty during treatment procedures.

In other examples, device 200 may include additional temperature sensors, such as three, four, or more temperature sensors.

Figure 7:
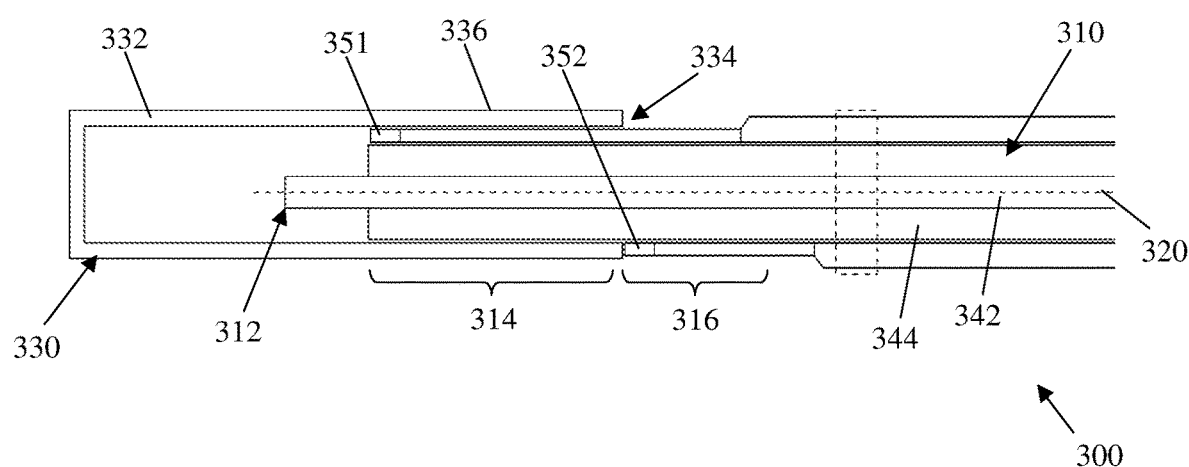
FIG. 7 illustrates a cross-sectional view of a further example device for interstitial laser therapy, from a front-side perspective.

Referring to FIG. 7, there is illustrated a further example device 300 for interstitial laser therapy. Device 300 includes an optical waveguide 310 extending about a central longitudinal axis 320 and having an optical output end 312. Device 300 further includes an optical diffuser 330 optically coupled to, or optically associated with, or positioned about, output end 312. Diffuser 330 includes a housing 332 having an open end 334 for receiving output end 312 and a first longitudinal portion 314 of optical waveguide 310. Housing 332 has an exterior surface 336. Device 300 further includes a first temperature sensor 351, interposed, positioned or located between central longitudinal axis 320 and exterior surface 336 within the longitudinal extent of first longitudinal portion 314 of optical waveguide 310, and a second temperature sensor 352, fixed to optical waveguide 310. As previously, in another example, first temperature sensor 351 can be positioned internally of an exterior surface 336 of the optical diffuser 330.

Optical waveguide 310 includes an inner layer 342 and an outer layer 344 radially surrounding inner layer 342. First temperature sensor 351 is fixed to outer layer 344 of first longitudinal portion 314. Second temperature sensor 352 is fixed within a second longitudinal portion 316 of optical waveguide 310. Second temperature sensor 352 is fixed to outer layer 344 of second longitudinal portion 316. First and second longitudinal portions 314 and 316 are not stripped, or shaved, of outer layer 344. This configuration may facilitate manufacturing, or assembling, of device 300.

Housing 332 should be provided with an inner diameter which exceeds an outer diameter of optical waveguide 310, in order to accommodate first temperature sensor 351.

Figure 8:
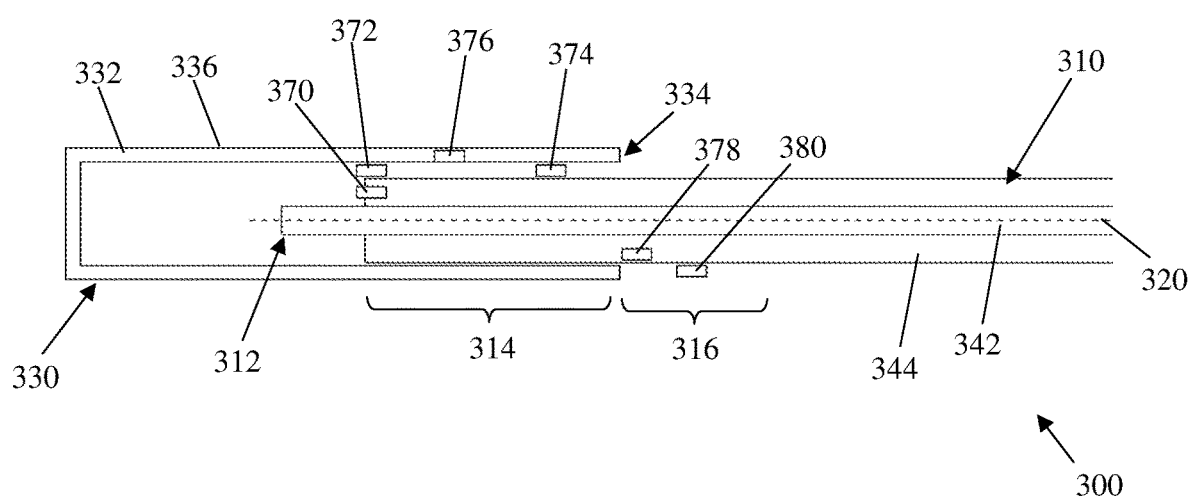
FIG. 8 illustrates a simplified schematic of the device of FIG. 7, showing various placements for a first temperature sensor and a second temperature sensor.

Referring to FIG. 8, there is illustrated a simplified schematic of device 300 showing various, alternative points or positions, where a first temperature sensor and a second temperature sensor, or additional temperature sensors, may be arranged, positioned, embedded or located, either individually or collectively.

In one example, first temperature sensor 370 is embedded in outer layer 344 of first longitudinal portion 314, and is partially exposed towards, or in the vicinity of, output end 312. In another example, the first temperature sensor may be completely embedded in outer layer 344. In another example, first temperature sensor 372 is positioned on outer layer 344 of first longitudinal portion 314, and projects, or protrudes towards output end 312. In another example, first temperature sensor 374 is positioned on outer layer 344 of first longitudinal portion 314, and is displaced from an extremity of first longitudinal portion 314 nearest to output end 312. For example, first temperature sensor 364 may be positioned in the vicinity of open end 334. In another example, first temperature sensor 376 is positioned within a groove, recess, or cavity of housing 332. In other examples, outer layer 344 and housing 332 may both be provided with a corresponding groove, recess, or cavity for accommodating first temperature sensor 376. In other examples, the first temperature sensor may be embedded, positioned, arranged, or located within a cladding layer of inner layer 342 in first longitudinal portion 314, and arranged without obstructing the propagation of electromagnetic waves in a core layer of inner layer 342.

In one example, second temperature sensor 378 is embedded in outer layer 344 of second longitudinal portion 316. In other examples, second temperature sensor 378 may be only partially embedded in outer layer 344 of second longitudinal portion 316. In another example, second temperature sensor 380 is positioned on outer layer 344 of second longitudinal portion 316, and is offset, displaced, or removed from housing 332 and open end 334. The distance between second temperature sensor 380 and open end 334 may vary in various embodiments. In other examples, the second temperature sensor may be embedded, positioned, arranged, or located within a cladding layer of inner layer 342 in second longitudinal portion 316, and arranged without obstructing the propagation of electromagnetic waves in a core layer of inner layer 342.

In various further examples, two or more of any of the first temperature sensors 351, 370, 372, 374 and 376 can be used. In another example, two or more of any of the second temperature sensors 352, 378 and 380 can be used.

System for Interstitial Laser Therapy

Figure 9:
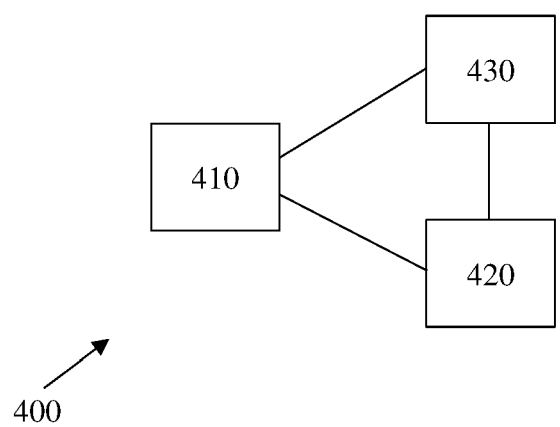
FIG. 9 illustrates an example system for interstitial laser therapy.

Referring to FIG. 9, there is illustrated an example system 400 for interstitial laser therapy. System 400 comprises a device 410 for interstitial laser therapy, as described in any of the previous examples. System 400 further comprises a power tunable optical source 420 optically coupled to an input end of an optical waveguide of device 410, and a processing system 430. Processing system 430 is configured to obtain one or more temperature measurements from one or more temperature sensors of device 410, and to adjust an optical output power of optical source 420.

Optical source 420 delivers an optical signal to the optical waveguide and permits the tuning, or adjustment, of the optical signal's power. In some examples, optical source 420 is a laser or an LED, or other device capable of generating an optical signal. In other examples, optical source 420 is a power-tunable active device, such as an amplifier, or a power tunable passive device, such as an attenuator or tunable coupler, which relays an optical signal (generated from another optical source) to the optical waveguide of device 410.

In some examples, processing system 430 receives, or obtains, the one or more temperature measurements directly from the one or more temperature sensors of device 410. In other examples, processing system 430 receives, or obtains, the one or more temperature measurements from one or more peripheral devices connected to the one or more temperature sensors, where the peripheral devices calculate the temperatures of one or more tissues being treated based on sensor data acquired from the one or more temperature sensors. Example peripheral devices include voltmeters, power meters, spectrometers, or any other instrument for interpreting sensor data and converting it to a temperature measurement. In yet other examples, processing system 430 calculates the temperature of the tissue being treated based on sensor data acquired from the one or more temperature sensors.

Processing system 430 relies on the temperature measurement to determine how to adjust the output optical power of optical source 420. In some examples, processing system 430 may rely on additional information, or data, in determining how to adjust the output optical power of optical source 420. This additional information may include the size and dimensions of a tumour being treated, as well as the type of tissue of the tumour. This information may be determined using medical imaging devices prior to treatment commencing. In some examples, processing system 430 may rely on data tables including optical power/energy requirements, exposure/radiation times, and optical wavelength requirements for particular tissues or tumours in determining how to adjust the output optical power of optical source 420.

System 400 may further include a channel for delivering device 410 to a treatment region. Examples for a channel include a catheter, a cannula, a tube, or any other channel depending on the location of the tumour or tissue being treated (for example, liver, pancreas, prostate, brain, or any other location within a patient's body). The channel may be inserted into the body of a patient. Device 410 would be inserted into the channel, with a diffuser of device 410 as the leading portion, and with the optical waveguide of device 410 being subsequently fed through the channel. The channel would thus guide device 410 to the treatment region.

In a further example, the channel, i.e. the cannula, can be provided with a clear end portion and/or a closed trocar tip (or other type of sharp-pointed instrument). A cannula with a clear end portion allows for laser energy and/or heat to be transmitted out from the cannula into the tissue. Traditional trocars are solid, and are commonly formed of opaque plastic or metal. Traditional trocars also do not have a closed end.

In one example, a trocar is used that has a sharp end which can be used to penetrate tissues like a normal cannula. The sharp end can cut and pierce tissue and/or skin. The end portion of the channel, i.e. the cannula, is preferably made of a transparent material, an optically clear material or an optically semi-opaque material. Optionally, the complete length of the cannula can be made of the same material (the transparent material, the optically clear material or the optically semi-opaque material). That is, at least in some examples, at least an end portion of the channel, i.e. the cannula, is transparent or semi-opaque. These examples allow laser energy and/or heat to penetrate through the walls of the cannula into surrounding tissues. In another optional form, the cannula also can be provided with an irrigation outlet and an irrigation inlet if used with an irrigation fluid.

System 400 may further include an imaging device for locating device 410 as it is being delivered to the treatment region. Example imaging devices include MRI scanners, ultrasound scanners, or other echolocation scanners. An advantage of device 410 is that it is able to measure the temperature of a tissue being treated without the need for additional diagnostic devices. This allows for the use of a simpler imaging device, such as an ultrasound scanner which is normally not able to measure temperature, for locating device 410 during therapy.

Advantageously, system 400 provides a feedback mechanism which enables accurate monitoring of the temperature level of a tumour or tissue being treated and adjustment of this temperature level by means of adjusting the output optical power delivered to the tumour or tissue. This feedback procedure can be executed in real time (or with low latency) due to the reduced complexity of the elements used. That is, it is no longer necessary to employ highly complex MRI scanners to merely estimate the temperature.

Processing System

Figure 10:
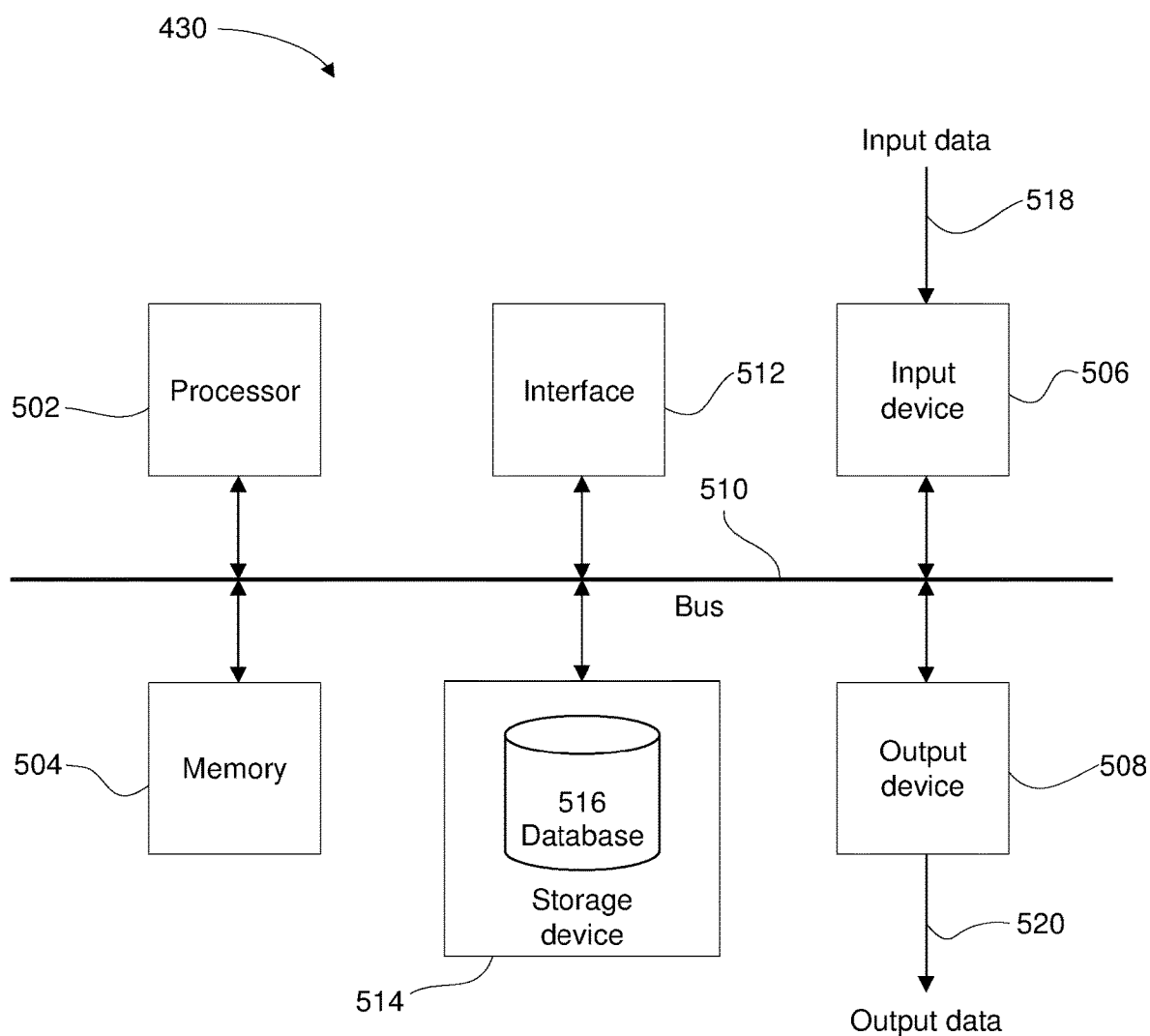
FIG. 10 illustrates an example processing system for use in the system of FIG. 9.

Referring to FIG. 10, there is illustrated an example processing system 430. In particular, the processing system 430 generally includes at least one processor 502, or processing unit or plurality of processors, memory 504, at least one input device 506 and at least one output device 508, coupled together via a bus or group of buses 510. In certain embodiments, input device 506 and output device 508 could be the same device. An interface 512 can also be provided for coupling the processing system 430 to one or more peripheral devices, for example interface 512 could be a PCI card or PC card. At least one storage device 514 which houses at least one database 516 can also be provided. The memory 504 can be any form of memory device, for example, volatile or non-volatile memory, solid state storage devices, magnetic devices, etc. The processor 502 could include more than one distinct processing device, for example to handle different functions within the processing system 430.

Input device 506 receives input data 518, for example temperature readings or data from one or more of the temperature sensors, and can include, for example, a keyboard, a pointer device such as a pen-like device or a mouse, audio receiving device for voice controlled activation such as a microphone, data receiver or antenna such as a modem or wireless data adaptor, data acquisition card, etc. Input data 518 could come from different sources, for example keyboard instructions in conjunction with data received via a network. Output device 508 produces or generates output data 520 and can include, for example, a display device or monitor in which case output data 520 is visual, a printer in which case output data 520 is printed, a port for example a USB port, a peripheral component adaptor, a data transmitter or antenna such as a modem or wireless network adaptor, or data sent to control or adjust the output optical power of optical source 420, etc. Output data 520 could be distinct and derived from different output devices, for example a visual display on a monitor in conjunction with data transmitted to a network. A user could view data output, or an interpretation of the data output, on, for example, a monitor or using a printer. The storage device 514 can be any form of data or information storage means, for example, volatile or non-volatile memory, solid state storage devices, magnetic devices, etc.

In use, the processing system 430 is adapted to allow data or information to be stored in and/or retrieved from, via wired or wireless communication means, the at least one database 516. The interface 512 may allow wired and/or wireless communication between the processing unit 502 and peripheral components that may serve a specialised purpose. The processor 502 receives instructions as input data 518 via input device 506 and can display processed results or other output to a user by utilising output device 508. More than one input device 506 and/or output device 508 can be provided. It should be appreciated that the processing system 430 may be any form of terminal, server, specialised hardware, or the like.

Further Examples

The following examples provide a more detailed discussion of particular embodiments. The examples are intended to be merely illustrative and not limiting to the scope of the present invention.

In any of the examples previously discussed, the diffuser, or a part of the diffuser, can be, optionally, additionally provided with one or more holes, one or more slits, one or more openings, and/or one or more vents. For example, one or more holes, slits, openings and/or vents can be used to enable a better diffusion of the electromagnetic energy, e.g. laser energy, out from the laser fibre. This advantageously results in a reduction in damaging the diffuser tip as well as better penetration of energy into the tissues.

Traditionally, laser diffuser tips are solid and clear or semi-opaque to enable the laser energy diffuse out. This causes heating of the diffuser. The diffuser can overheat and disintegrate as a result of the laser energy power. The tissue to which the laser energy is delivered may also tend to char and burn, rather than more gradually heat-up and allow the energy to penetrate into the tissue.

In further examples, the one or more holes, the one or more slits, the one or more openings, and/or the one or more vents in the diffuser additionally allow gases generated from the tissue being heated to escape out, diffuse out, or vent, from the inside region of the diffuser, and again enable a more consistent energy transfer into the tissue. That is, in use generated gases escape out from an inside region of the optical diffuser via the one or more holes, the one or more slits, the one or more openings, and/or the one or more vents.

A particular advantageous use of an "open", "non-solid", or "semi-closed" diffuser is that if used with irrigation solution to cool the diffuser, the irrigation solution has a much better and easier access to the diffuser. This allows the diffuser to be cooled more efficiently and enables higher laser power to be used without causing damage to the diffuser or resulting in charring or burning of the tissue. Additionally, this can also simultaneously allow gases released from heating of the tissue, or from the irrigation solution, to escape out, diffuse out, or vent, more readily from the inside region of the diffuser.

A variety of types, shapes, number, orientations and/or configurations of one or more holes, one or more slits, one or more openings, and/or one or more vents can be utilised.

Figure 11:
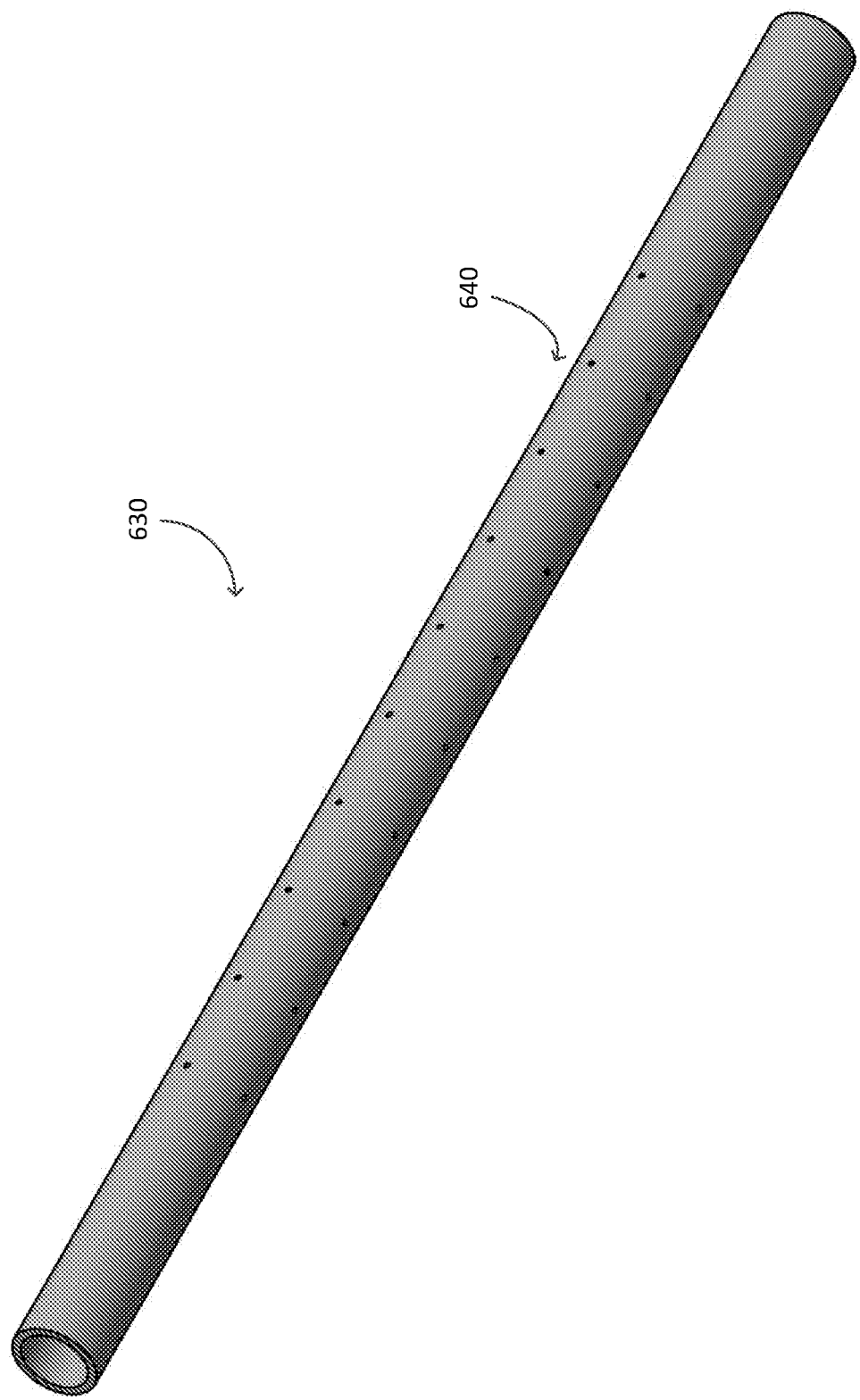
FIG. 11 illustrates an example optical diffuser.

Referring to FIG. 11, there is shown an example optical diffuser, preferably being a cylindrical optical diffuser 630 (or a tubular optical diffuser). The relative length, thickness and diameter of optical diffuser 630 is provided by way of example only, as is the orientation, location and extent of one or more holes 640. One or more holes 640, i.e. one or more openings and/or one or more vents, are provided along at least part of the longitudinal length of optical diffuser 630, and at different circumferential positions, and pass through the housing of optical diffuser 630 to extend from an exterior surface to an interior surface of optical diffuser 630.

Figure 12:
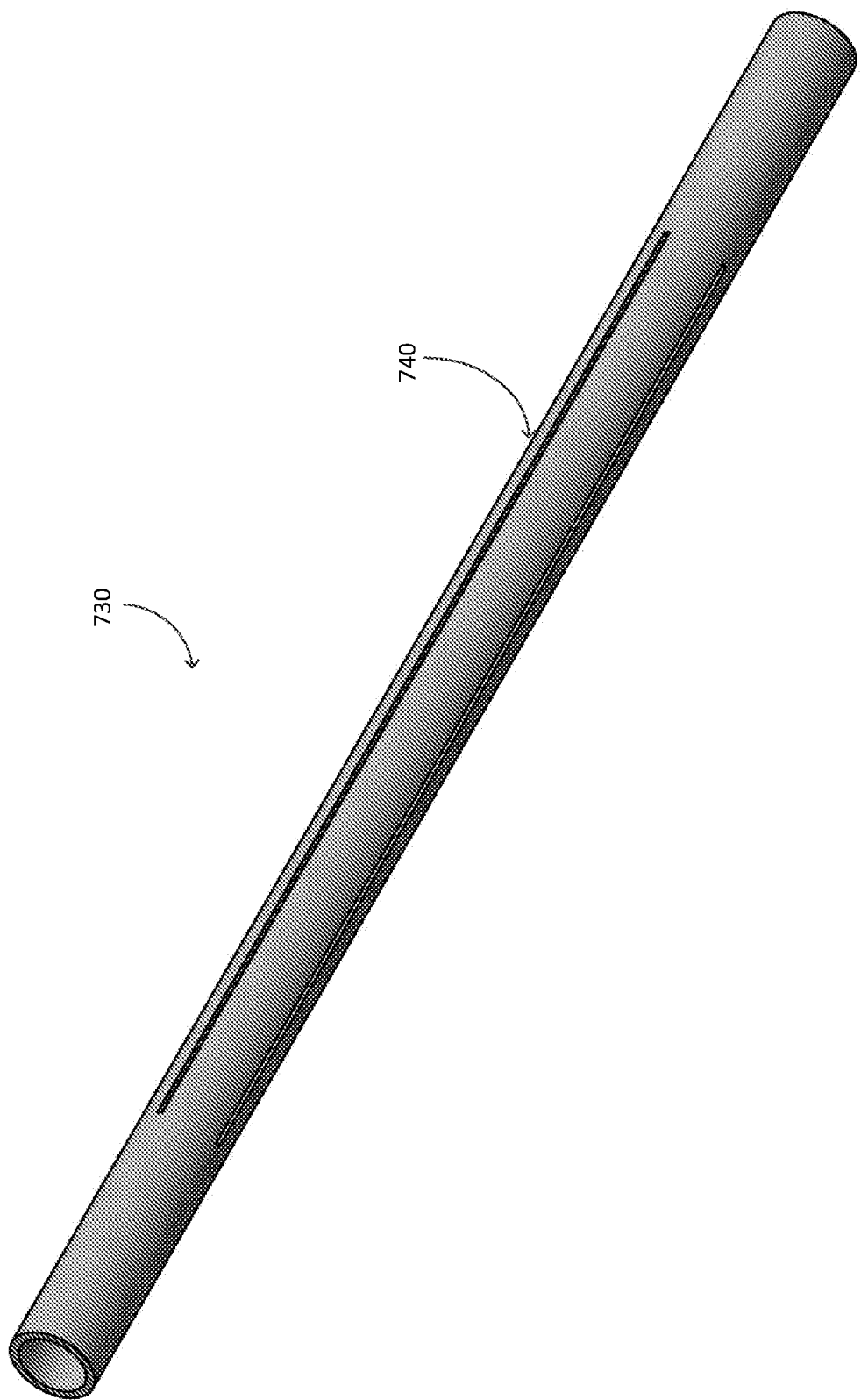
FIG. 12 illustrates another example optical diffuser.

Referring to FIG. 12, there is illustrated another example optical diffuser 730 provided with one or more slits 740, i.e. one or more openings 740 and/or one or more vents 740. One or more slits 740, i.e. one or more openings and/or one or more vents, are provided along at least part of the longitudinal length of optical diffuser 730, and at different circumferential positions, and pass through the housing of optical diffuser 730 to extend from an exterior surface to an interior surface of optical diffuser 730. More than one slit can be provided along a longitudinal length of optical diffuser 730.

It should be appreciated that the one or more holes, one or more slits, one or more openings and/or one or more vents, illustrated by way of example in FIGS. 11 and 12, can be provided along any length, portion, extent or circumference of the example diffusers. A variety of different types of holes, slits, openings and/or vents can be provided. Similarly, a variety of different shapes of holes, slits, openings and/or vents can be provided. Additionally, any number of holes, slits, openings and/or vents can be provided as part of a diffuser. Additionally, a variety of orientations for holes, slits, openings and/or vents can be provided as part of a diffuser. Additionally, a variety of configurations of a mixture of holes, slits, openings and/or vents can be provided as part of a diffuser.

As illustrated by way of example in FIGS. 11 and 12, one or more holes, one or more slits, one or more openings and/or one or more vents can be positioned about the circumference of a diffuser, as well as being positioned along at least part of a longitudinal extent or length of the diffuser. Any desired number of holes, slits, openings and/or vents can be positioned about the circumference with any desired angular spacing. As non-limiting examples, provided by way of indication only, holes, slits, openings and/or vents may have a length or diameter of from about 0.1 mm to about 10 mm. Holes, slits, openings and/or vents could be spaced apart for example by about 0.5 mm to about 10 mm. Longitudinally extending lines or patterns of holes, slits, openings and/or vents can be spaced about 90 degrees apart circumferentially, assuming four longitudinally extending lines or patterns are desired. Longitudinally extending lines or patterns of holes, slits, openings and/or vents can be spaced about 120 degrees apart circumferentially, assuming three longitudinally extending lines or patterns are desired. Longitudinally extending lines or patterns of holes, slits, openings and/or vents can be spaced about 180 degrees apart circumferentially, assuming two longitudinally extending lines or patterns are desired. In another example, one longitudinally extending line or pattern of holes, slits, openings and/or vents is provided, assuming one longitudinally extending line or pattern is desired.

Figure 13:
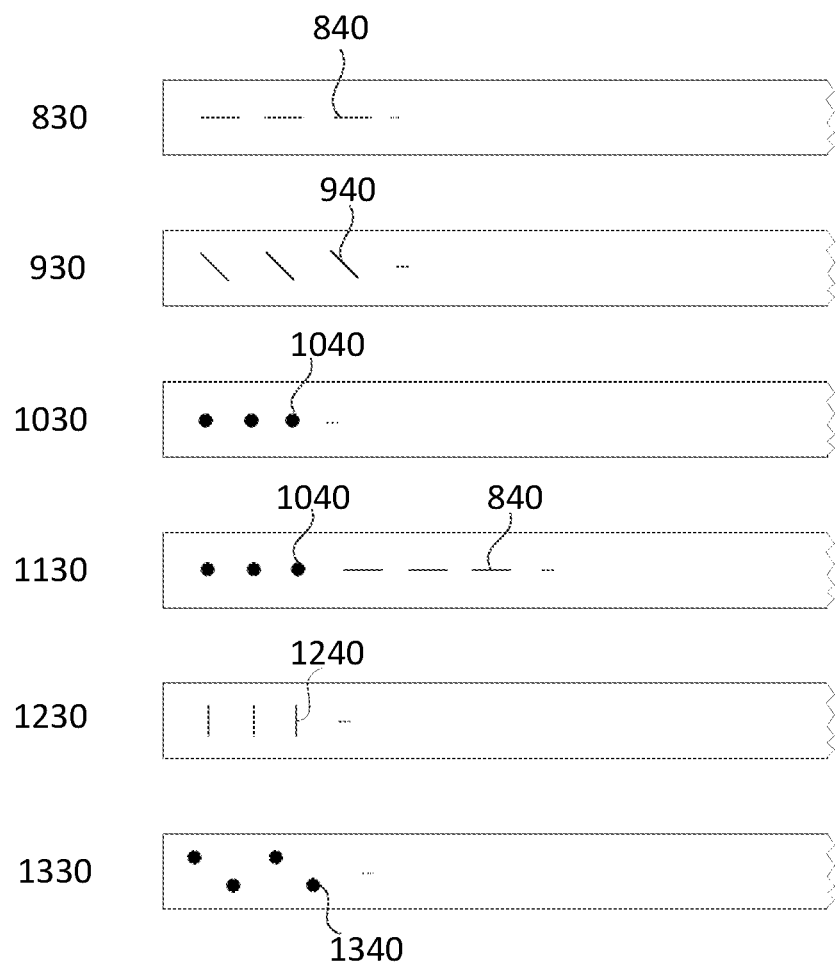
FIG. 13 illustrates further example optical diffusers.

Referring to FIG. 13, there are illustrated side-views of further example optical diffusers 830, 930, 1030, 1130, 1230, 1330, having different example types, shapes, orientations and/or configurations of holes, slits, openings and/or vents. The example optical diffusers are illustrated as being of indefinite longitudinal extent. The example optical diffusers are tube shaped or cylindrical in three-dimensions. Diffuser 830 includes one or more longitudinally aligned slits or vents 840. Diffuser 930 includes one or more angled slits or vents 940. Diffuser 1030 includes one or more holes or vents 1040. Diffuser 1130 includes a combination of one or more holes or openings together with one or more slits 840. The configuration, orientation and/or arrangement of different shapes of holes, openings, vents or slits can be significantly varied. Diffuser 1230 includes perpendicularly aligned one or more slits 1240. Diffuser 1330 includes one or more holes or openings 1340 that are offset at different or periodic circumferential (or radial) angles at least partially along the longitudinal extent or length of diffuser 1330. It should be realised that the number of holes, slits, openings and/or vents shown in example diffusers is for illustration only and any number can be utilised, for example one, two, three, four, five, six, seven, eight, nine, ten, etc. holes, slits, openings and/or vents can be utilised, or any combination thereof.

Figure 14:
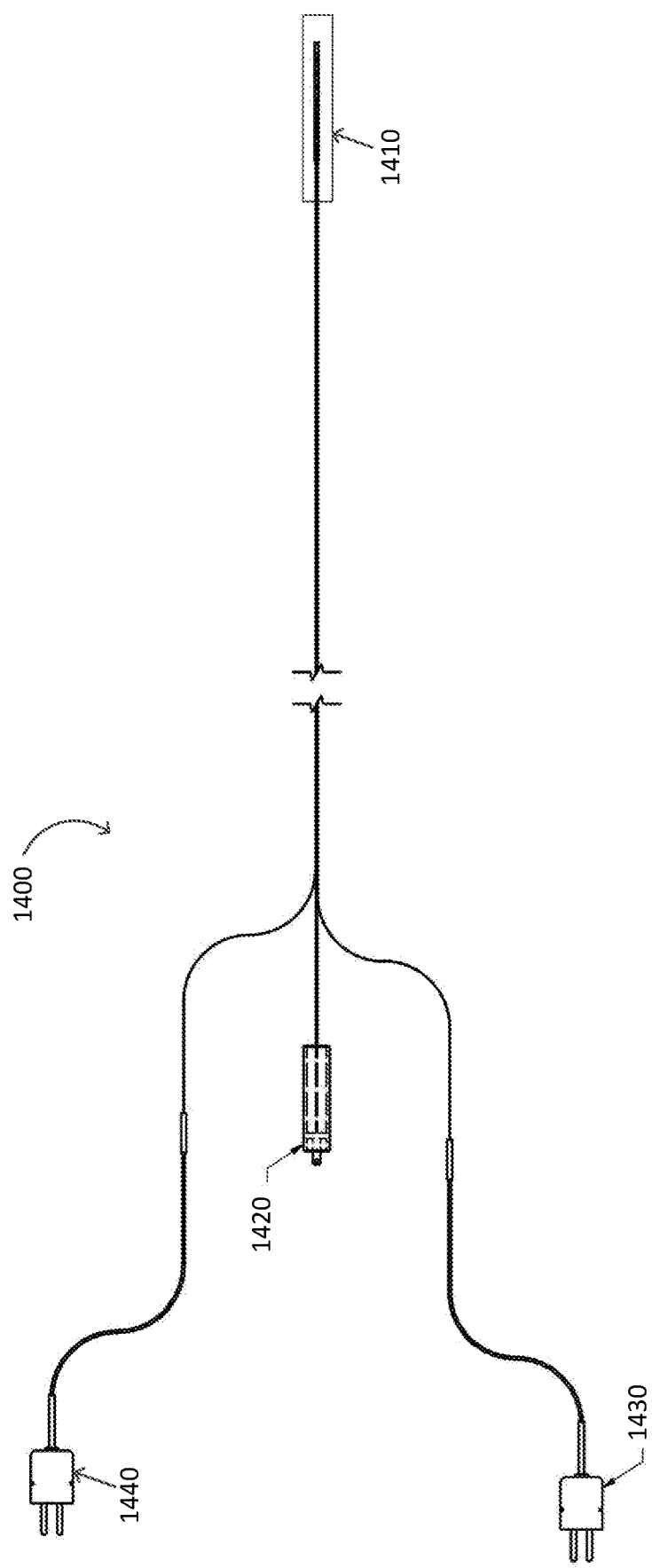
FIG. 14 illustrates an example system or assembly for interstitial laser therapy.

FIG. 14 illustrates part of an example system or assembly 1400 for interstitial laser therapy. System or assembly 1400 includes an optical diffuser (and other components) assembly section 1410, a connector 1420 for a laser fibre, a connector 1430 for a first thermocouple (i.e. a first temperature sensor), and a connector 1440 for a second thermocouple (i.e. a second temperature sensor).

Figure 15:
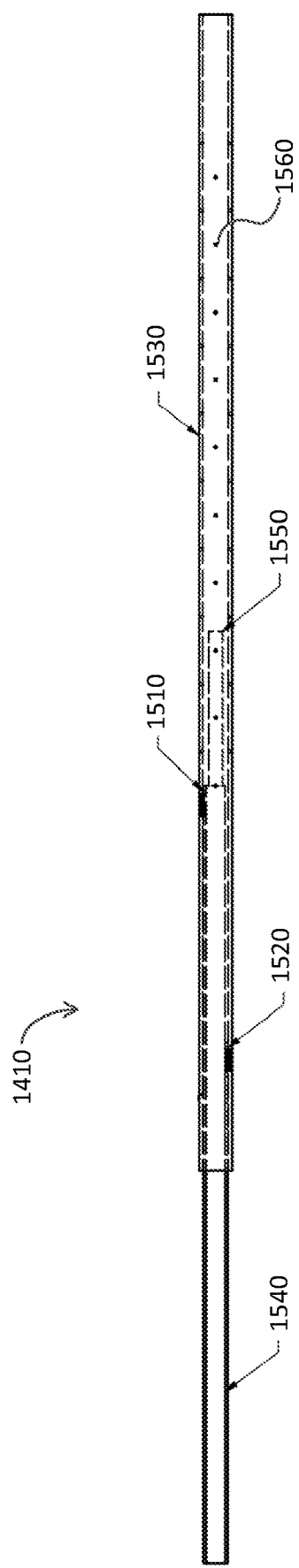
FIG. 15 illustrates an example device for use in an example system or assembly for interstitial laser therapy.

FIG. 15 illustrates further details of the optical diffuser (and other components) assembly section 1410. Optical diffuser 1530 attaches to laser fibre (with jacket) 1540. A first thermocouple 1510 (i.e. first temperature sensor) and optionally a second thermocouple 1520 (i.e. second temperature sensor) can be provided. Also illustrated is laser fibre 1550, preferably with a clear silica tip. Optical diffuser 1530 can be glued or otherwise attached (e.g. frictionally fitted) onto laser fibre 1540. One or more holes, openings, and/or vents 1560 can be provided as part of optical diffuser 1530.

Figure 16:
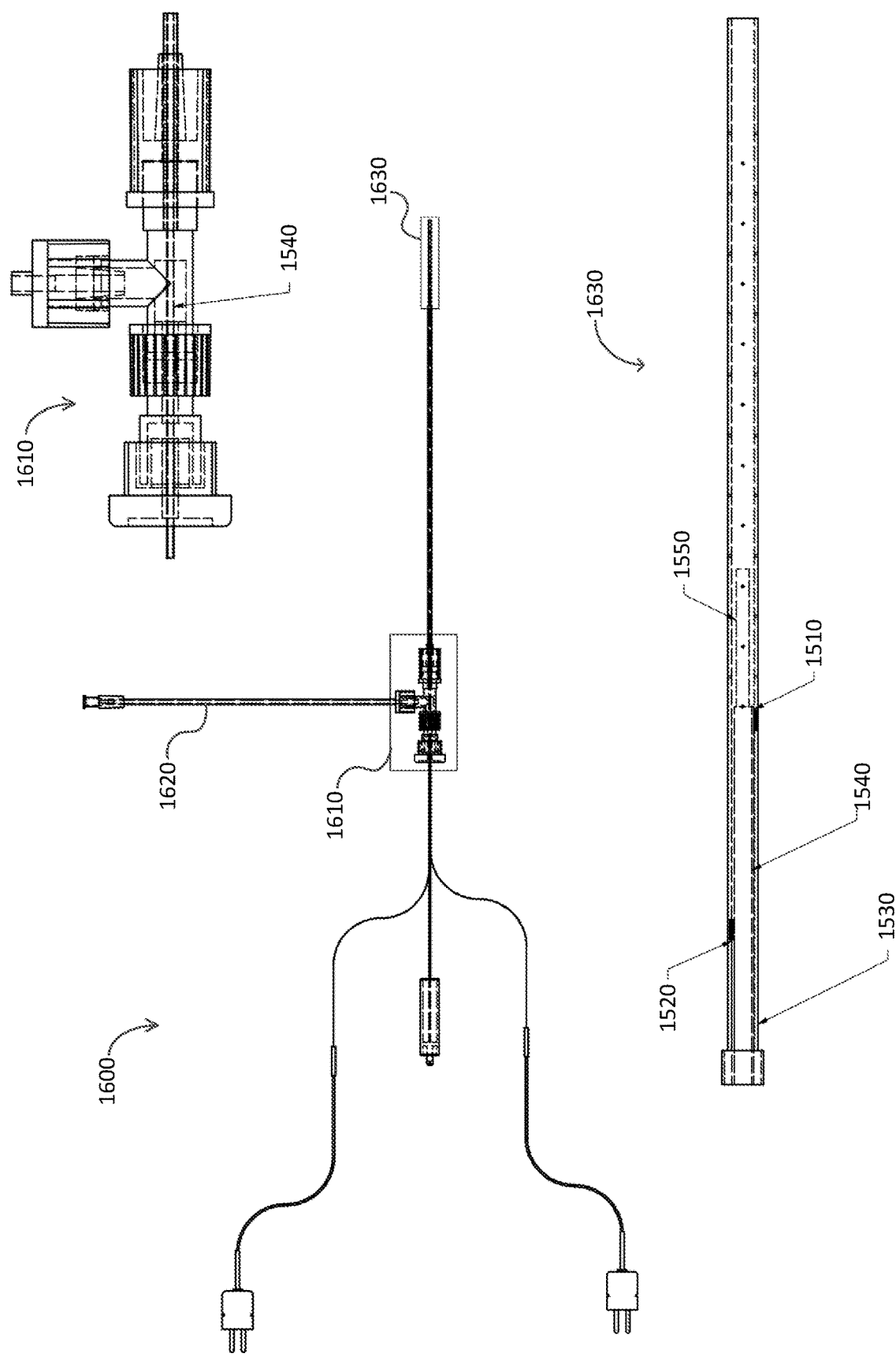
FIG. 16 illustrates another example system or assembly for interstitial laser therapy.

FIG. 16 illustrates another example system or assembly 1600 for interstitial laser therapy. Connectors 1610, which can be a variety of types or configurations, are used for connecting tubes or pipes transporting cooling fluid. The cooling fluid can be introduced by input pipe or tubing 1620, through connectors 1610, to be directed to operational zone 1630 (i.e. about the optical diffuser section). Operational zone 1630 includes optical diffuser 1530, first thermocouple 1510 (i.e. first temperature sensor), second thermocouple 1520 (i.e. second temperature sensor), laser fibre (with jacket) 1540 as at least part components. Laser fibre 1540, and thermocouples (i.e. temperature sensors), can be inserted through connectors 1610, or at least some of connectors 1610, into jacket tubing.

Figure 17:
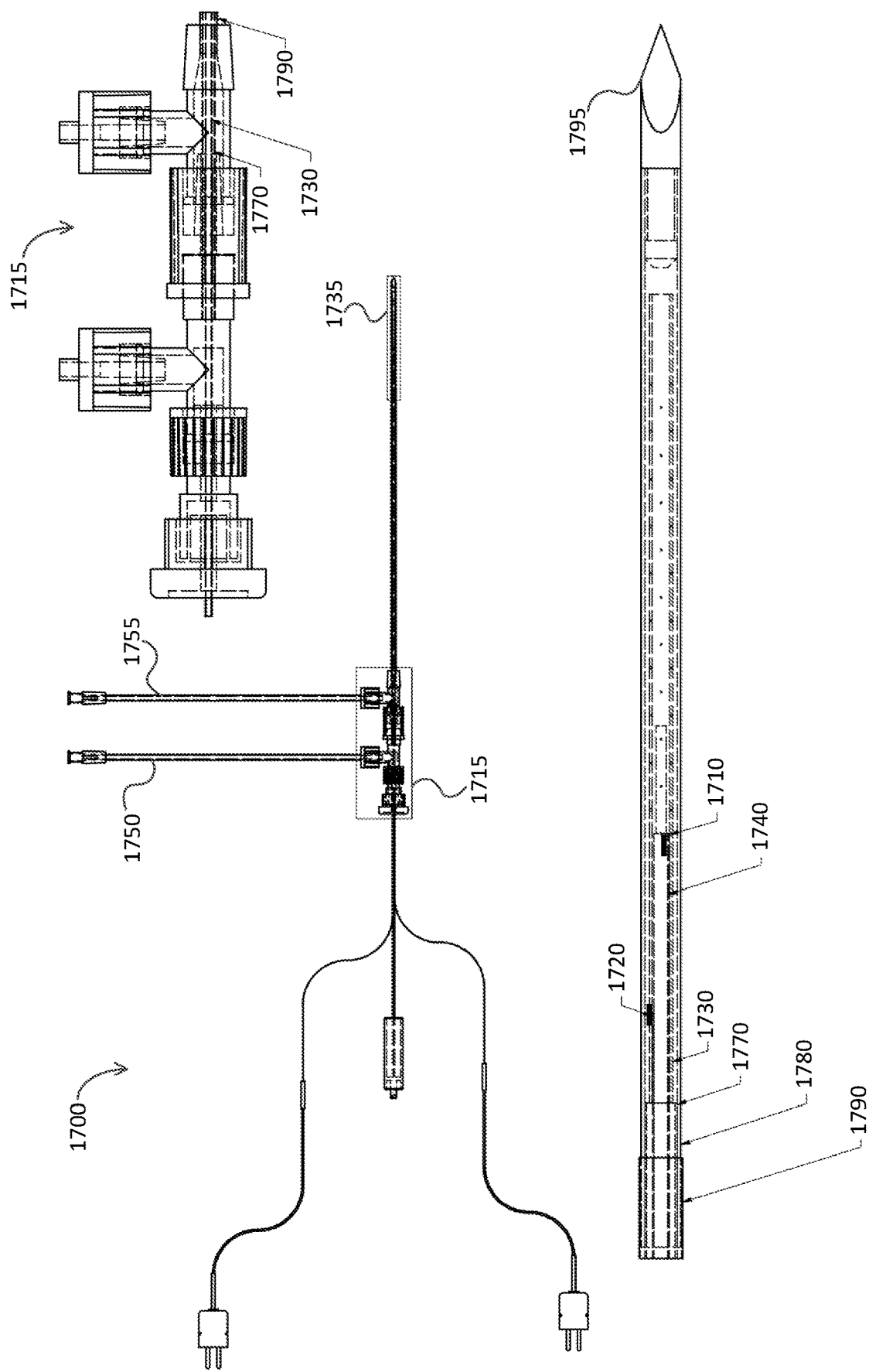
FIG. 17 illustrates another example system or assembly for interstitial laser therapy.

FIG. 17 illustrates another example system or assembly 1700 for interstitial laser therapy. Connectors 1715 include an arrangement of connectors for introducing or transporting cooling fluid to operational zone 1735 via first inlet/outlet tube or pipe 1750 and second inlet/outlet tube or pipe 1755. In operational zone 1735 (i.e. about the optical diffuser section) there is provided optical diffuser 1730, first thermocouple 1710 (i.e. first temperature sensor), second thermocouple 1720 (i.e. second temperature sensor), laser fibre (with jacket) 1740 and jacket tubing 1770. Also provided is an introducer first section 1780, in this example being clear or transparent tubing, and an introducer second section 1790, in this example being metallic tubing. Trocar 1795, or other form of sharp instrument, is provided at an end.

In other examples, the introducer, i.e. the channel or the cannula, can be provided with a clear end portion and/or a closed trocar tip. An introducer, or channel or cannula, with a clear end portion allows for laser energy and/or heat to be transmitted out from the introducer, or cannula, into the tissue. The trocar has a sharp end which can be used to penetrate tissues like a normal cannula. In an example, a cannula can be used having a trocar tip that is provided as a transparent tip or a semi-opaque tip. An end portion of the introducer, or channel or cannula, can be made of a transparent material, an optically clear material or an optically semi-opaque material. Optionally, the complete length of the introducer, or channel or cannula, can be made of the same material (i.e. the transparent material, the optically clear material or the optically semi-opaque material). These examples allow laser energy and/or heat to penetrate through the walls of the introducer, or channel or cannula, into surrounding tissues. As illustrated, the introducer, or cannula, can be provided with fluid or irrigation inlets/outlets if used with a cooling or irrigation fluid. In other examples the introducer, or channel or cannula, could be opaque, for example made of metal or ceramic.

The introducer (i.e. the channel or the cannula), or the end portion thereof, and the trocar (i.e. a puncturing spike section or region, or a metallic spike) can be transparent, optically clear or optically semi-opaque, and together can function as a combined, or integrated, trocar-diffuser device or unit. That is, the trocar can function similarly to, and/or complimentary with, the optical diffuser. The trocar (i.e. a puncturing spike section or region, or a metallic spike) can also act as an optical diffuser (or part of an optical diffuser), at the same time as acting as a trocar. That is, the trocar has a dual function. In such an example, the trocar is optically coupled to, or is optically associated with, an optical output end of an optical waveguide, similarly as described previously for the optical diffuser. The trocar can also be provided with an inlet for irrigation fluid.

Figure 18:
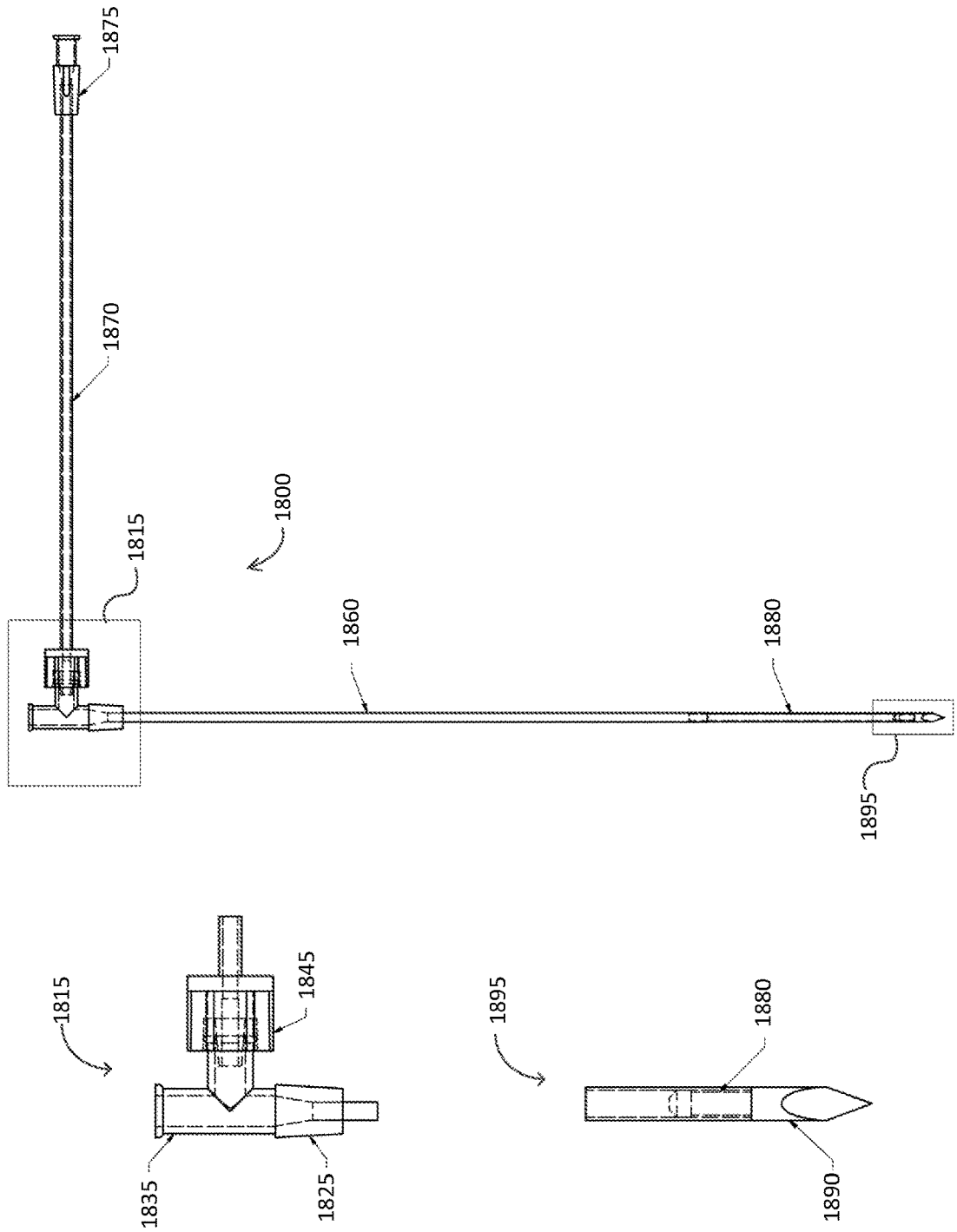
FIG. 18 illustrates an example introducer for use in an example system or assembly for interstitial laser therapy.

FIG. 18 illustrates another example system or assembly 1800 for interstitial laser therapy. Connectors 1815, for example including a T-connector, can include a male luer slip port 1825, and a female luer lock 1835 which is connected to a male luer cap 1845 and which includes a fluid extension line or pipe. System or assembly 1800 includes trocar section 1895, or puncturing spike section, which includes a metallic spike 1890, or other cutting edge, which can be glued, or otherwise attached to clear or transparent tubing 1880. Clear or transparent tubing 1880 provides a suitable clear or transparent window or region for correct laser operation. Tubing 1860, which can be metallic for example, connects connectors 1815 to clear or transparent tubing 1880.

In another example, there may not be any metallic tubing 1860 and instead clear or transparent tubing 1880 may extend between connectors 1815 and trocar section 1895, or puncturing spike section. Fluid transmission extension line or pipe 1870 connects to female luer lock 1875 which provides an exit port for cooling fluid. System or assembly 1800 includes an "introducer", i.e. a cannula, which includes one or more hollow tubes or pipes, having a trocar tip, i.e. spike. The hollow tube or pipe is closed off at a distal end. A stiffening rod, i.e. a "stiffener", can be placed through the middle of the introducer, or cannula, for example during the initial stages of establishing a portal through tissue. A jacket tube can be provided which is a stiffening tube or pipe and which houses the assembly of the laser fibre, one or more thermocouples (i.e. one or more temperature sensors) and the optical diffuser, so as to allow these components to be inserted into the introducer.

Figure 19:
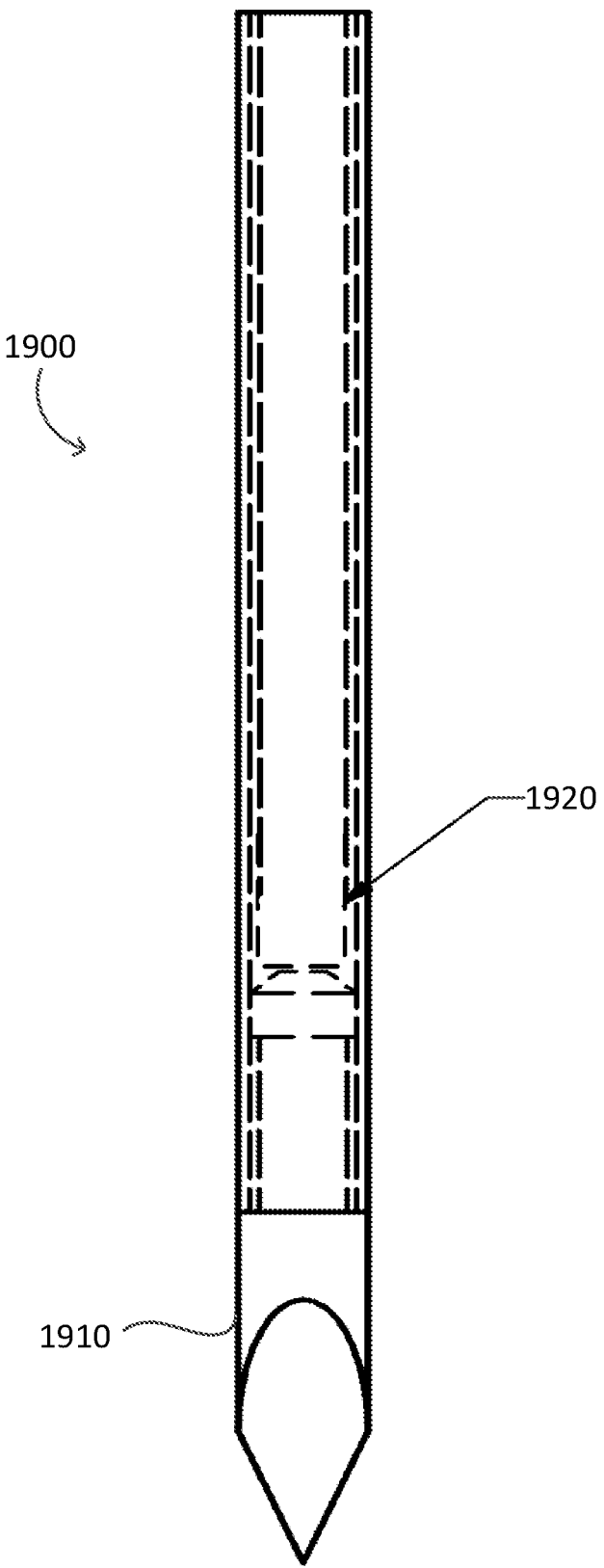
FIG. 19 illustrates an example trocar section including a stiffener and a spike for use in an example system or assembly for interstitial laser therapy.

FIG. 19 shows a distal end part for a trocar section 1900, i.e. a puncturing spike section or region, having a metallic spike 1910 or other form of cutting and/or piercing edge. Also illustrated is stiffener 1920. In different examples an end of stiffener 1920 can be touching or abutting an internal end of metallic spike 1910 (as illustrated) or an end of stiffener 1920 can be spaced apart from an internal end of metallic spike 1910.

Figure 20:
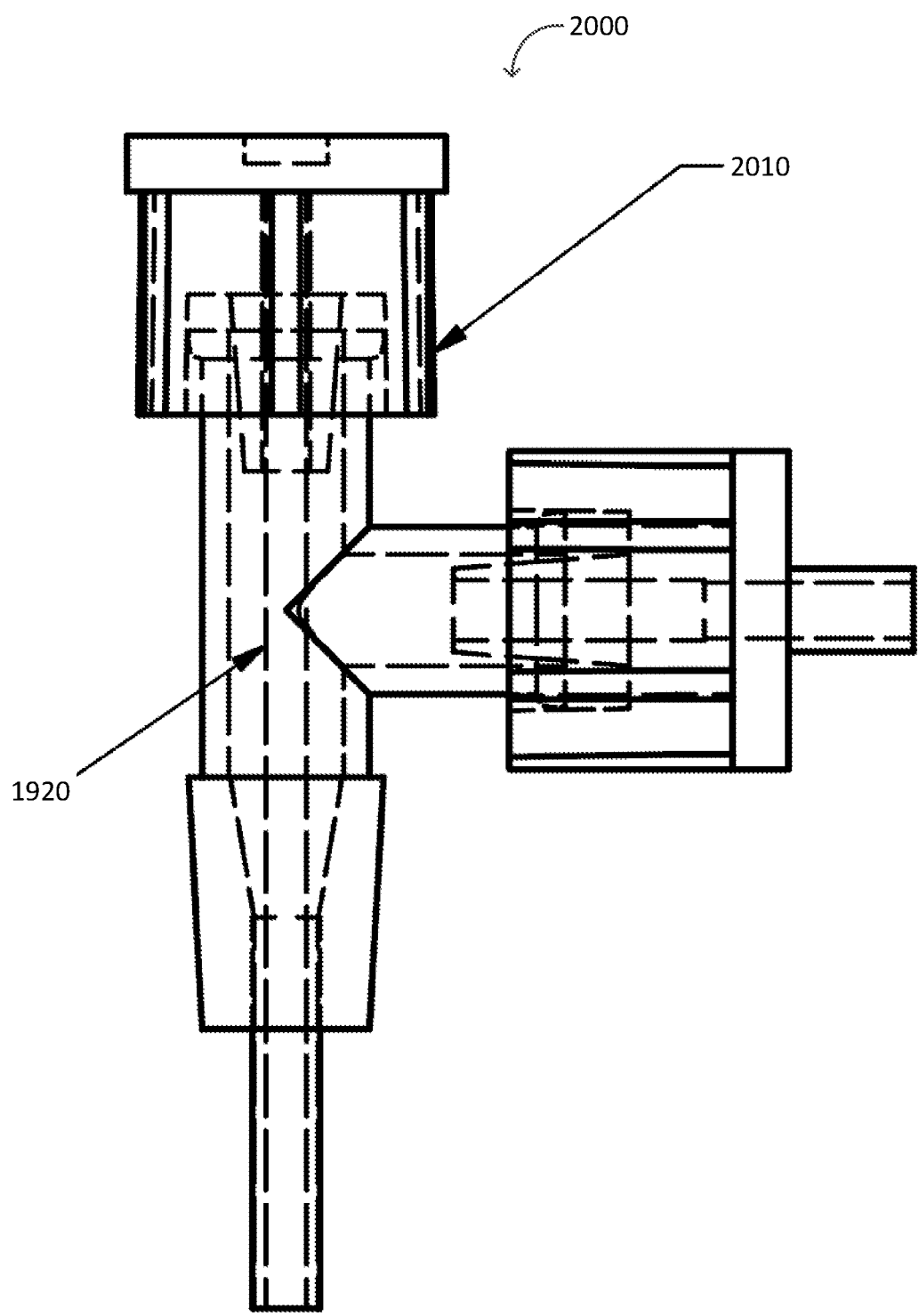
FIG. 20 illustrates example connectors and a stiffener position.

FIG. 20 illustrates example connectors 2000 and stiffener 1920. Stiffener 1920, for example a stiffening rod, can be inserted into the introducer, i.e. cannula. Male luer cap 2010 from stiffener 1920 locks onto a female luer lock. In one example the introducer can include an opaque tube (e.g. a metallic tube) longitudinally extending part way along its length and a clear tube, or a transparent tube, or a clear window, provided or longitudinally extending near a distal end of the introducer. In another example, the introducer could be a length of tube that is entirely transparent, clear or semi-opaque material.

Optional embodiments may also be said to broadly include the parts, elements, steps and/or features referred to or indicated herein, individually or in any combination of two or more of the parts, elements, steps and/or features, and wherein specific integers are mentioned which have known equivalents in the art to which the invention relates, such known equivalents are deemed to be incorporated herein as if individually set forth.

Although a preferred embodiment has been described in detail, it should be understood that many modifications, changes, substitutions or alterations will be apparent to those skilled in the art without departing from the scope of the present invention.

The invention claimed is:

1. A system for interstitial laser therapy, the system comprising:
   a device for interstitial laser therapy comprising:
      an optical waveguide extending along a central longitudinal axis and having an optical output end;
      an optical diffuser optically coupled to the optical output end and extending along the central longitudinal axis,
         wherein the optical diffuser comprises a housing having an open end for receiving the optical output end and a first longitudinal portion of the optical waveguide, and
         wherein the optical diffuser is provided with one or more holes, one or more slits, one or more openings, and/or one or more vents; and
      a first temperature sensor interposed between the central longitudinal axis and an exterior surface of the housing within a longitudinal extent of the first longitudinal portion of the optical waveguide;
   a power-tunable optical source optically coupled to the optical waveguide; and
   a processing system configured to:
      obtain a temperature measurement from the first temperature sensor; and
      adjust an optical output power of the optical source.

2. The system of claim 1, wherein the first temperature sensor is interposed between the first longitudinal portion of the optical waveguide and the housing.

3. The system of claim 1, wherein the housing is a tubular housing.

4. The system of claim 3, wherein an outer diameter of the housing is greater than or equal to an outer diameter of the optical waveguide.

5. The system of claim 3, wherein an inner diameter of the housing is greater than or equal to an outer diameter of the optical waveguide.

6. The system of claim 1, wherein gases generated during use escape out from an inside region of the optical diffuser and an irrigation fluid cools the optical diffuser via the one or more holes, the one or more slits, the one or more openings, and/or the one or more vents.

7. The system of claim 1, wherein the first temperature sensor is selected from the group of a micro-temperature sensor, an integrated temperature sensor, a thermocouple, and an infrared temperature sensor.

8. The system of claim 1, wherein the optical waveguide is an optical fibre.

9. The system of claim 1, wherein the device further comprises a second temperature sensor, attached to the optical waveguide within a second longitudinal portion of the optical waveguide.

10. The system of claim 1, wherein the first temperature sensor is positioned adjacent to or abutting an internal surface of the optical diffuser.

11. The system of claim 1, further comprising a cannula for delivering the device to a treatment region.

12. The system of claim 11, wherein at least an end portion of the cannula is transparent or semi-opaque.

13. The system of claim 11, wherein the cannula includes an irrigation inlet to receive an irrigation fluid.

14. The system of claim 13, wherein the irrigation fluid is transported to an operational zone which includes the optical diffuser.

15. The system of claim 14, wherein the irrigation fluid exits the cannula at an outlet such that an ablation zone from laser energy is limited in extent to beyond the outlet by the irrigation fluid.

16. The system of claim 11, further including a stiffener inserted into the cannula.

17. The system of claim 11, wherein the cannula includes or is attached to a trocar or a sharp end.

18. The system of claim 17, wherein the trocar is transparent or semi-opaque and is optically coupled to the optical output end, such that the trocar provides a further optical diffuser.

19. The system of claim 17, wherein the trocar has a closed end and the trocar includes an irrigation inlet to receive an irrigation fluid.

20. A system for interstitial laser therapy comprising:
a device for interstitial laser therapy comprising:
   an optical waveguide extending along a central longitudinal axis and having an optical output end;
   an optical diffuser optically coupled to the optical output end and extending along the central longitudinal axis, wherein:
   the optical diffuser comprises a housing having an open end for receiving the optical output end and a first longitudinal portion of the optical waveguide, and
   the optical diffuser is provided with one or more holes, one or more slits, one or more openings, and/or one or more vents;
a first temperature sensor interposed between the central longitudinal axis and an exterior surface of the housing within a longitudinal extent of the first longitudinal portion of the optical waveguide; and
a second temperature sensor attached to the optical waveguide within a second longitudinal portion of the optical waveguide
a power-tunable optical source optically coupled to the optical waveguide; and
a processing system configured to:
   obtain temperature measurements from the first temperature sensor and from the second temperature sensor; and
adjust an optical output power of the optical source.

21. The system of claim 20, wherein the second temperature sensor is arranged adjacent to the open end of the optical diffuser.

22. The system of claim 20, wherein the first temperature sensor and the second temperature sensor are adapted to measure a temperature difference.

23. The system of claim 20, wherein the second temperature sensor is adapted to measure a second temperature external to the optical diffuser.

24. The system of claim 20, wherein the central longitudinal axis does not intersect with the first temperature sensor and/or the second temperature sensor.

25. The system of claim 20, wherein the first temperature sensor and/or the second temperature sensor are/is positioned apart from the optical output end.

26. The system of claim 20, wherein the second temperature sensor is positioned outside the longitudinal extent of the optical diffuser.

* * * * *